(12) United States Patent
Acey

(10) Patent No.: US 7,273,962 B2
(45) Date of Patent: Sep. 25, 2007

(54) COMPOSITIONS AND METHODS FOR REMOVING HEAVY METALS FROM CONTAMINATED SAMPLES USING MEMBRANES PROVIDED WITH PURIFIED METALLOTHIONEIN (MT) PROTEINS

(75) Inventor: Roger A. Acey, Long Beach, CA (US)

(73) Assignee: MGP Biotechnologies, LLC, Irvine, CA (US)

( * ) Notice: Subject to any disclaimer, the term of this patent is extended or adjusted under 35 U.S.C. 154(b) by 164 days.

(21) Appl. No.: 11/255,427

(22) Filed: Oct. 19, 2005

(65) Prior Publication Data

US 2006/0063959 A1    Mar. 23, 2006

Related U.S. Application Data

(60) Continuation-in-part of application No. 10/797,748, filed on Mar. 9, 2004, now Pat. No. 7,135,605, which is a division of application No. 09/948,495, filed on Sep. 6, 2001, now Pat. No. 6,750,056.

(60) Provisional application No. 60/620,528, filed on Oct. 19, 2004.

(51) Int. Cl.
*A62D 3/00* (2006.01)
*B09C 1/08* (2006.01)
*C12M 1/00* (2006.01)

(52) U.S. Cl. .................. 588/315; 261/1; 405/128.5; 435/289.1; 588/412

(58) Field of Classification Search ................ None
See application file for complete search history.

(56) References Cited

U.S. PATENT DOCUMENTS

| | | | |
|---|---|---|---|
| 5,441,643 A | 8/1995 | Spears et al. | |
| 5,500,353 A | 3/1996 | Smit et al. | |
| 5,567,316 A | 10/1996 | Spears et al. | |
| 5,665,865 A | 9/1997 | Lerner et al. | |
| 5,679,548 A | 10/1997 | Barbas et al. | |
| 5,814,480 A | 9/1998 | Hillman et al. | |
| 5,824,512 A | 10/1998 | Pazirandeh et al. | |
| 6,391,590 B1 * | 5/2002 | Sano et al. | 435/69.7 |
| 6,451,260 B1 | 9/2002 | Dusterhoft et al. | |
| 6,750,042 B2 * | 6/2004 | Summers et al. | 435/69.1 |
| 2003/0105304 A1 | 6/2003 | Acey et al. | |

FOREIGN PATENT DOCUMENTS

| | | |
|---|---|---|
| EP | 0 557 042 | 2/1993 |
| JP | 2003082422 | 3/2003 |
| WO | 2003/022868 | 3/2003 |
| WO | PCT US02/17273 | 6/2003 |

OTHER PUBLICATIONS

Chen et al., "Hg2+ removal by genetically engineered *Escherichia coli* in a hollow fiber reactor," Biotechnol.Prog.; (1998) 14, 5, 667-71.*

Bae et al., "Enhanced bioaccumulation of heavy metals by bacterial cells displaying synthetic phytochelatins," Biotechnology and Bioengineering, (Dec. 5, 2000), 70/5 (518-524).*

Brook et al., Purification of metallothionein-like metal binding proteins from Artemia. Molecular Biology of the Cell. 1994, vol. 5, No. Suppl, p. 226A, Abstract No. 1316

Chen et al., The induction and extraction of metallothioneins in Artemia. Chinese Journal of Oceanology and Limnology. 1994, vol. 12, No. 2 pp. 175-179, especially pp. 177-178.

Fischer et al., Recent excitement regarding metallothionein. Proceeding of the National Academy of Sciences USA. 1998, vol. 95 pp. 333-334.

Hamer, Metallothionein. Annual Review of Biochemistry. 1985, vol. 55, pp. 913-951.

"NOTICE" regarding publication developed under Grant No. CX824823 awarded by the U.S. EPA.

Pedersen et al., Primary structures of decapod crustacean metallothioneins with special emphasis on freshwater and semi-terrestrial species. Biochemistry Journal 1996, vol. 319, pp. 999-1003.

Ma et al., Recent Developments for in situ treatment of metal contaminated soils. Prepared for U.S. EPA by PRC Management Inc., dated Mar. 5, 1997 and published on web site at http://www.clu-in.org//download/remed/metals2.pdf.

Evanko et al., Remediation of metals—contaminated soils and groundwater. Technology Evaluation Report prepared for GWRTAC dated Oct. 1997.

Valls et al., Engineering a mouse metallothionein on the cell surface of *Ralstonia europha* CH34 for immobilization of heavy metals in soil. Nature Biotechnology. 2000, vol. 18 pp. 661-665.

Del Ramo et al., Effect of cadmium pre-exposure in cadmium accullation by brine shrimp Artemia: involvement of low-molecular-weight cadmium-binding ligands. Marine Environmental Research 1993 vol. 5. pp. 29-33.

Sode et al., Construction of a marine cyanobacterial strain with increased heavy metal ion tolerance by introducing exogenic metallothionein gene. Journal of Marine Biotechnology 1998 vol. 6 pp. 174-177.

Brook et al., Purification of metallothionein-like metal binding proteins from Artemia. Molecular Biology of the Cell. 1994, vol. 5, No. Suppl, p.226A, Abstract No. 1316.

Chen et al., The induction and extraction of metallothioneins in Artemia. Chinese Journal of Oceanology and Limnology. 1994, vol. 12, No. 2 pp. 175-179, especially pp. 177-178.

(Continued)

*Primary Examiner*—Robert A Wax
(74) *Attorney, Agent, or Firm*—Louis C. Cullman; Michelle S. Glasky; Kirkpatrick & Lockhart Preston Gates Ellis LLP

(57) ABSTRACT

Devices, such as solid supports having metal binding proteins, such as metallothionein proteins, bound thereto are disclosed for removing metals from substrates in need of having such metals removed therefrom. Specifically membranes having metallothionein proteins from the brine shrimp *Artemia* are disclosed for removing metals from liquid substrates. Associated methods for removing metals from substrates using metallothionein proteins are also disclosed.

19 Claims, 6 Drawing Sheets

OTHER PUBLICATIONS

Fischer et al., Recent excitement regarding metallothionein. Proceeding of the National Academy of Sciences USA. 1998, vol.95 pp. 333-334.

Hammer, Metallothionein. Annual Review of Biochemistry. 1986, vol. 55, pp. 913-951.

"Notice" regarding publication developed under Grant No. CX824823 awarded by the U.S. EPA.

Pedersen et al., Primary structures of decapod crustacean metallothioneins with special emphasis on freshwater and semi-terrestrial species. Biochemistry Journal 1996, vol. 319, pp. 999-1003.

Ma et al., Recent Developments for in situ treatment of metal contaminated soils. Prepared for U.S. EPA by PRC Management Inc., dated Mar. 5, 1997 and published on web site at http://www.clu-in.org//download/remed/metals2.

Evanko et al., Remediation of metals-contaminated soils and groundwater. Technology Evaluation Report prepared for GWRTAC dated OCT., 1997.

Valls et al., Engineering a mouse metallothionein on the cell surface of Ralstonia europha CH34 for immobilization of heavy metals in soil. Nature Biotechnology. 2000, vol. 18 pp. 661-665.

Del Ramo et al., Effect of cadmium pre-exposure in cadmium accululation by brine shrimp Artemia: Involvement of low-molecular-weight cadmium-binding ligands. Marine Environmental Research 1993 vol. 5, pp. 29-33.

Sode et al., Construction of a marine cyanobacterial strain with increased heavy metal ion tolerance by introducing exogenic metallothionein gene. Journal of Marine Biotechnology 1998 vol. 6 pp. 174-177.

Chen et al. "Hg2+ removal by genetically engineered Escherichia coli in a hollow fiber reactor," Biotechnol. Prog. 14:667-71, 1998.

Bae et al. "Enhanced bioaccumulation of heavy metals by bacterial cells displaying synthetic phytochelatins," Biotechnology and Bioengineering. 70:518-524, 2000.

* cited by examiner

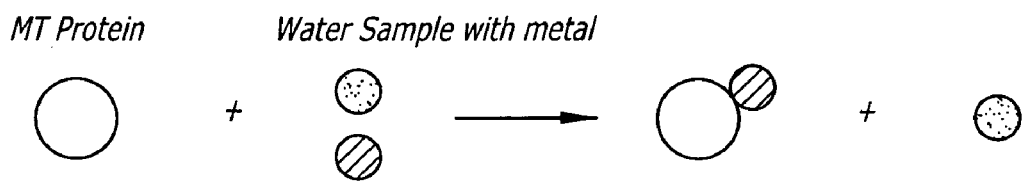
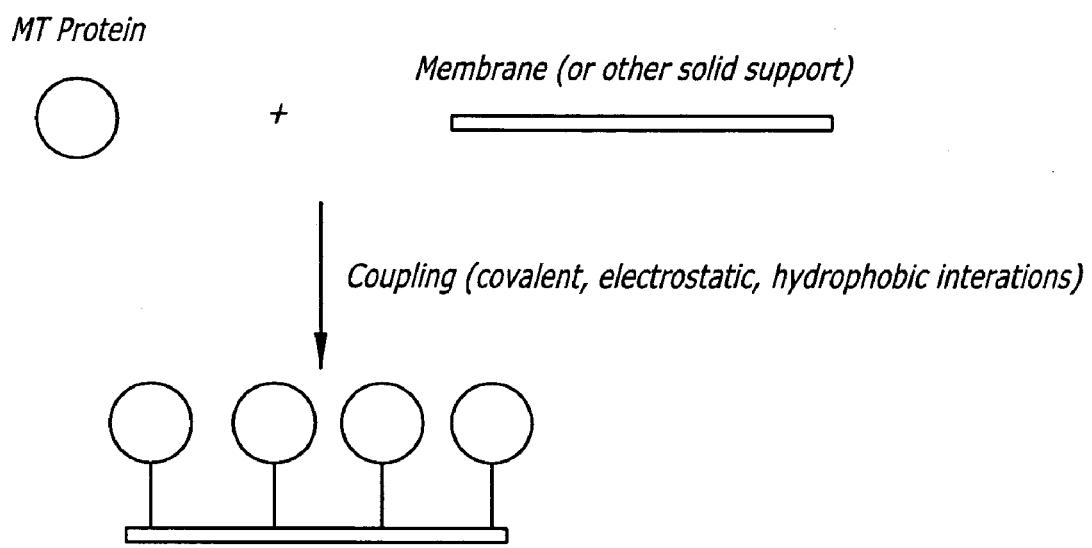
FIG. 3
FIG. 4

⊘ Toxic Metals such as cadmium and mercury

⊙ Required metals such as magnesium and calcium

Water Supply

FIG. 8

```
                      (1)  1         10        20        30        40
           Artemia    (1)  ---------------MDCCK-----NGCTCA-PNCKCA-------
            Rabbit    (1)  ---------------MDP-NCSCA-TRDSCACA-SSCKCKE-----
             Human    (1)  ---------------MDP-NCSCA-AGDSCTCA-GSCKCKE-----
      Green Monkey    (1)  ---------------MDP-NCSCA-TGVSCTCA-DSCKCKE-----
   Channel Catfish    (1)  ---------------MDP--CECS-KTGTCNCG-TSCKCSN-----
African Clawed Frog   (1)  --------------MDPQDCKCE-TGASCSCG-TTCSCSN------
       Blue Mussel    (1)  PGPCNCIETNVCICGTG-CS-G---KCCRCG-DACKCA--------
  Painted Sea Urchin  (1)  -----------MPGPDVKCFCCRDGKECACGGGECCITG-------
         Fruit Fly    (1)  ---------------------------MVCK--GCGTN--------
         C. elegans   (1)  -----------------VCK-------CDCKNQNCSCNTGT----
              Rice    (1)  ----------------MSCSCG---SSCSCG-SNCSCGKKYPDLE
             Wheat    (1)  ----------------MSCNCG---SGCSCG-SDCKCGKMYPDLT
             Yeast    (1)  ANDCKCPN----GCSCPNCA-N---GGCQCG-DKCECK--------

(46) 46        60        70        80
           Artemia   (46)  KDCKC-----CKG-CECKSNPECK---------CEKNCS------
            Rabbit   (46)  --CKCTSCKKSCCSCCPAGCTKCA---------QGCICKG-----
             Human   (46)  --CKCTSCKKSCCSCCPVGCAKCA---------QGCICKG-----
      Green Monkey   (46)  --CKCTSCKKSCCSCCPVGCAKCA---------QGCVCKG-----
   Channel Catfish   (46)  --CQCACCKKSCCSCCPSGCSKCA---------SGCVCKG-----
African Clawed Frog  (46)  --CKCTSCKKSCCSCCPAECSKCS---------QGCHCEK-----
       Blue Mussel   (46)  SGCGCSG---CKVVCKCS--GTCK---------CGCDCTGPT-NC
  Painted Sea Urchin (46)  --KCCKEGDRTCCGKCSNAACKCA---------DGCKCEGA--CA
         Fruit Fly   (46)  --CQCSAQKCGDNCACNKDC-------------QCVCKN------
         C. elegans  (46)  KDCDCSDAKCCEQYCCPTASEKKC---------CKSGCAG---GC
              Rice   (46)  EKSSSTK---ATVVLGVAPEKKAQ--QFEAAAESGETAHGCS---
             Wheat   (46)  EQGSAAAQVAAVVVLGVAPENKAG--QFEVAA--GQSGEGCS---
             Yeast   (46)  -KQSCHG---CGEQCKCGS--------------HGSSCHG---SC

(91) 91        100       110
           Artemia   (91)  -CNS-CGCH------------------    SEQ ID NO. 11
            Rabbit   (91)  -ALDKCSCCA-----------------    SEQ ID NO. 12
             Human   (91)  -ASDKCSCCA-----------------    SEQ ID NO. 13
      Green Monkey   (91)  -ASEKCNCCA-----------------    SEQ ID NO. 14
   Channel Catfish   (91)  -DTCDSKCCQ-----------------    SEQ ID NO. 15
African Clawed Frog  (91)  -GSKKCSCCN-----------------    SEQ ID NO. 16
       Blue Mussel   (91)  KCESGCSCK------------------    SEQ ID NO. 17
  Painted Sea Urchin (91)  CTMGNCTC-------------------    SEQ ID NO. 18
         Fruit Fly   (91)  --GPKDQCCSNK---------------    SEQ ID NO. 19
         C. elegans  (91)  KCAN-CECAQ--------------AAH    SEQ ID NO. 20
              Rice   (91)  -CGSSCRCNPCNC--------------    SEQ ID NO. 21
             Wheat   (91)  -CGDNCKCNPCNC--------------    SEQ ID NO. 22
             Yeast   (91)  GCGDKCECK------------------    SEQ ID NO. 23
```

COMPOSITIONS AND METHODS FOR REMOVING HEAVY METALS FROM CONTAMINATED SAMPLES USING MEMBRANES PROVIDED WITH PURIFIED METALLOTHIONEIN (MT) PROTEINS

CROSS REFERENCE TO RELATED APPLICATIONS

This application claims priority under 35 U.S.C. §119(e) to U.S. Provisional Application Ser. No. 60/620,528 filed Oct. 19, 2004 and is a continuation-in-part of U.S. patent application Ser. No. 10/797,748 which is a divisional application of U.S. patent application Ser. No. 09/948,795 now U.S. Pat. No. 6,750,056, which are both incorporated by reference herein in their entirety.

FIELD OF THE INVENTION

The present invention relates to compositions and methods for removing heavy metals from contaminated samples. More specifically the present invention relates to removing heavy metals from contaminated samples using solid supports having metallothionein proteins bound thereto.

BACKGROUND OF THE INVENTION

Metal recovery and metal remediation and the associated need for efficient and safe methods for clean up of metal waste is a continuing environmental and business concern due to the toxicity and potential risk to human health posed by metal contaminants, as well as the economic value of precious heavy metals. Indeed, as the discharge of toxic wastes from agricultural, industrial and other commercial operations continues, the need for effective, safe and low-cost metal remediation methods increases. In a recent report by the United States Environmental Protection Agency (US EPA), metal contamination remains and historically has been a key concern at many contaminated sites (US EPA Work Assignment #011059, Mar. 5, 1997, Contract #68-W5-0055). In addition, there are numerous published reports of damage to wildlife, livestock, plant life as well as danger to human health as a result of metal poisoning from contaminated soil or waste matter (Impact of Lead-Contaminated Soil on Public Health by Xintaras, C. May 1992 at http://www.atsdr.cdc.gov/cxlead.html). For example, a primary concern to humans is the health hazard created by lead (Pb) contamination. Exposure to lead can occur through a variety of methods such as by ingestion of lead from food, water, soil, or even inhalation of dust. Lead poisoning is extremely dangerous and potentially fatal, with symptoms including seizures, mental retardation and behavioral disorders. Therefore, methods for metal remediation are extremely valuable both for their protection of our environment as well as for protection from diseases.

Recovered metals from various waste, discard or recycling efforts provide immense economic value as well as augmenting environmental pollution control. Metal recovery can be from innumerable and varied sources such as from waste electronic devices (transistors, chips, transformers, bus bars, cathodes, and microprocessors, populated computer circuit boards PCBs, motherboards). Costs associated with hazardous disposal of industrial waste in the absence of metal reclamation are enormous. Therefore, metal recycling or reuse of metal extracted from scrap or discarded metal-containing items not only reduces the volume and cost of metal waste requiring specialized disposal and handling efforts, but the reclaimed metal can also be resold or reused to provide additional economic value.

Prior art attempts at treating metal contamination have traditionally employed cleanup technologies which consist primarily of physically removing and then disposing of contaminated matter. These methodologies are not only labor intensive and less efficient, but also carry a high expense associated with removal and disposal of large or bulk quantities of contaminated waste. Metal contamination is especially difficult to remediate because unlike other types of waste such as chemical or organic matter, metals cannot be directly destroyed or converted. For example, current technologies for remediating metal contaminated soils consist primarily of landfilling or soil excavation with physical or chemical separation of the metal contaminants. Treatment of contaminated ground water usually involves flushing, filtration or chemical extraction to remove the contaminating metals. As a result, the cost of soil or ground water remediation is high, ranging in the hundreds to thousands of millions of dollars in projected five-year costs per site (U.S. EPA, 1993).

In addition, the risk to humans and the environment from heavy metal contamination is not limited to soil or ground water, but also includes other sources such as industrial waste, sludge waste, wastewater, radioactive waste (such as radionuclides from research and medical waste) and mining waste. Depending on the physical and chemical form of the metal contaminant to be removed, as well as the cost-benefit analysis for a particular remediation approach, which of the existing technologies is better suited for a particular site will vary. However, due to the high cost of traditional cleanup technologies, there still remains a great need for a less-expensive, safe and effective heavy metal recovery and cleanup technology.

There are some technologies currently available for the recovery or remediation of heavy metal contaminated waste. In general, these technologies combine one or more of the following general approaches: isolation, immobilization, toxicity reduction, physical separation or extraction of metal contamination from a waste product. Isolation technologies utilize a containment strategy in an attempt to confine a contaminated site or area so as to prevent further spread of the toxic metal waste. Immobilization technologies reduce the mobility of metal contaminants and include systems which provide an impermeable barrier to separate underlying layers of soil (containing the metal contaminants) from the topsoil layer. Also used are physical barriers which restrict the flow of uncontaminated groundwater through a contaminated site. Additionally, there are toxicity reduction processes which generally use chemical or biological techniques to decrease the toxicity or mobility of metal contaminants. Included in toxicity reduction processes are biological treatment technologies, which apply newer biotechnical approaches.

Metal remediation is a relatively new application of biological treatment technologies and includes processes such as bioaccumulation, phytoremediation, phytoextraction, and rhizofiltration. All of these biological treatments use certain plants and microorganisms to remediate metals through either adsorption, absorption, or concentration of contaminating metal ions. For example, in bioaccumulation, plants or microorganisms actively take up and accumulate metals from contaminated surroundings.

In phytoremediation, specific plants that have developed the ability to selectively remove metal ions from soil are used. Such plants include certain "hyperaccumulator" species such as the alpine pennycrass plant, which is capable of accumulating metals at levels of 260 times greater than most plants before showing toxicity symptoms. Most hyperaccumulator plants, however, are very slow growing and have specific growth requirements. Some of these growth requirements are not conducive to the use of these plants at sites or in situations where metal recovery or remediation is needed. Furthermore, there are very few plant species known or available for recovery or remediation use. Therefore, given the persistent and high incidence of metal contamination at environmental and waste sites (about 75% of Superfund Sites contain metal ions as a form of contamination, U.S. EPA, 1996), more efficient methods and approaches for removing heavy metals from contaminated sources are still needed.

More recently, in an attempt to meet these needs, biotechnological approaches have been employed as an alternative strategy to metal recovery and remediation. Included in these biotechnology approaches are the use of tobacco plants that have been manipulated to express metallothionein genes (Maiti et al. Seed-transmissible expression of mammalian metallothionein in transgenic tobacco, Biochem Biophys Res Commun. 150(2):640-7,1988). Metallothioneins (MTs) are small metal binding proteins ubiquitously distributed throughout the animal kingdom. They have high metal binding affinities and are believed to be important in controlling the intracellular levels of free metal ions. However, little else is known about their function or biological purpose. Metallothioneins were first discovered in 1957 in horse tissue. Since then, they have been identified in species ranging from fungi and shellfish to mice and humans.

The structural features of MTs include a high cysteine composition and lack of aromatic amino acids. The cysteine residues are responsible for the protein's high affinity metal ion binding capabilities. In general, MTs have a high degree of amino acid sequence similarity. However, the proteins or known gene sequences encoding the proteins have been used primarily in either the research setting or in disease treatment methodologies.

Accordingly, one of the objects of the present invention is to provide novel metal binding proteins for the removal of metals from a variety of substrates. This technology would allow for the efficient, cost effective, safe and simple removal of heavy metals from environmental waste or other materials contaminated with heavy metal.

SUMMARY OF THE INVENTION

Metallothionein (MT) proteins are generally about 60-68 amino acid residues in size and have a high degree of sequence conservation among the different species. In contrast, MTs from brine shrimp (Artemia) are much smaller in size (about 48 amino acid residues) and have distinctly unique amino acid and DNA sequences. The metal binding proteins of the present invention are capable of high capacity and high affinity metal binding. This makes them particularly suitable for use in pollution control, metal recycling, metal mining and other metal recovery and metal remediation technologies.

These and other objects are achieved by the compositions and methods of the present invention which provide for the efficient and reliable sequestration of heavy metals from a variety of sources using a regenerative metal binding support comprised of at least one metal binding protein immobilized on a solid support. The metal binding proteins can be expressed and produced easily for purposes such as metal remediation, metal recycling, metal mining or other types of processes where binding of one or more heavy metals is desired.

In accordance with the teachings of the present invention, at least one substantially purified metal binding protein is provided. In one embodiment of the present invention the metal binding protein is from the brine shrimp (Artemia) and has the amino acid sequence of SEQ ID NO. 2 or SEQ ID NO. 4.

```
                                                        SEQ ID NO.2
MET ASP CYS CYS LYS ASN GLY CYS THR CYS ALA PRO ASN CYS LYS 15
CYS ALA LYS ASP CYS LYS CYS CYS LYS GLY CYS GLU CYS LYS SER 30
ASN PRO GLU CYS LYS CYS GLU LYS ASN CYS SER CYS ASN SER CYS 45
GLY CYS HIS 48

SEQ ID NO.4
MET ASP CYS CYS LYS ASN GLY CYS THR CYS ALA PRO ASN CYS LYS 15
CYS ALA LYS ASP CYS LYS CYS 22
```

In another embodiment of the present invention, the metal binding protein sequences incorporate one or more conservative amino acid substitutions of SEQ ID NO. 2 or SEQ ID NO. 4. It should be noted that while the metal binding proteins will be discussed in the context of metal recovery and metal remediation, the proteins are readily applicable to many other uses where removal, recovery or simply binding of heavy metals or heavy metal complexes is desired.

In further accordance with the teachings of the present invention, the novel metal binding proteins can be utilized as a naked composition or can be provided in association with a support, or other delivery system to aid in either the dispersal, handling, packaging or function of the metal binding proteins in metal recovery, metal remediation or metal binding processes as disclosed herein. Therefore, any of the metal binding proteins of the present invention can be coupled to a support such as a membrane filter, to form a regenerative metal binding support, through which metal containing fluids are brought into contact.

The present invention is particularly well suited for use in metal recovery, metal remediation or metal recycling processes and methods. These methods include contacting a metal binding protein of the present invention having an amino acid sequence analogous to at least one metal binding protein sequence from brine shrimp (Artemia) with a substrate or material having a concentration of at least one heavy metal in order to bind the metal to the metal binding protein; and then separating the bound metal from the substrate or material.

For example, the metal binding proteins, and devices comprising them, disclosed herein are useful in connection with the treatment of any substrate having a concentration of at least one metal, such as a heavy metal. As will be appreciated by those skilled in the art, such heavy metal containing substrates can be any environmental or industrial material such as ground water, drinking water, contaminated soil, waste, or the like, containing a concentration of metal. Similarly, the methods of the present invention are equally useful in treating industrial or municipal wastes containing metals that are desirable to remove. This broad utility makes the compositions and associated methods of the present invention particularly useful in a wide variety of circumstances.

The metal binding proteins of the present invention retain high binding affinity for heavy metals in a variety of conditions, making them particularly useful in situations where removal or recovery of heavy metals from a substrate or any metal containing or metal contaminated source is desired. The metal binding proteins and the associated methods of the present invention provide for the efficient, cost effective, and safe removal and recovery of heavy metals from a wide variety of substrates.

In one embodiment of the device of the present invention, a device for removing heavy metals from a substrate comprising: a regenerative metal binding support comprising a polymer membrane having associated therewith and at least one substantially purified metallothionein (MT) protein, or a portion thereof, from an organism selected from the group consisting of mammals, fish, mollusks, echinoderms, crustaceans, reptiles, nematodes, grains and yeast; wherein the regenerative metal binding support binds heavy metals thereby removing the heavy metals from the substrate; and the binding of heavy metal to the regenerative metal binding support is reversible and wherein the regenerative metal binding support is reusable.

In additional embodiments of the device of the present invention, the mammal is a human, a monkey or a rabbit; the fish is a catfish; the mollusk is mussel; the echinoderm is a sea urchin; the reptile is a frog, the grain is rice or wheat and the crustacean is a brine shrimp (*Artemia*).

In another embodiment of the device of the present invention, the MT protein has an amino acid sequence selected from the group consisting of SEQ ID NO. 2, SEQ ID NO. 4, SEQ ID NO. 11, SEQ ID NO. 12, SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 21 and SEQ ID NO. 23.

In yet another embodiment of the device of the present invention, the polymer membrane is nylon.

In still another embodiment of the device of the present invention, the substrate is a liquid.

In another embodiment of the device of the present invention, the heavy metal is a heavy metal complex.

In one embodiment of the method of the present invention, a method is provided for removing metals from a substrate comprising contacting a substrate having heavy metals therein with a regenerative metal binding support comprising a polymer membrane having associated therewith at least one substantially purified metallothionein (MT) protein, or a portion thereof, from an organism selected from the group consisting of mammals, fish, mollusks, echinoderms, crustaceans, reptiles, nematodes, grains and yeast; binding the heavy metal to the regenerative metal binding support thereby producing a substrate having less heavy metal contained therein.

In another embodiment of the method of the present invention, the polymer membrane is nylon.

In yet another embodiment of the method of the present invention, the heavy metal is a heavy metal complex.

In still another embodiment of the method of the present invention, the substrate is a liquid.

In another embodiment of the method of the present invention, the method further comprises releasing the bound heavy metal from the regenerative metal binding support; and regenerating the metal-binding capacity of the regenerative metal binding support.

BRIEF DESCRIPTION OF THE DRAWINGS

FIG. 3 illustrates metallothionein (MT) protein selectively binding heavy metals in solution in accordance with the teachings of the present invention.

FIG. 4 illustrates MT proteins coupled to a solid support in accordance with the teachings of the present invention.

FIG. 8 depicts the sequence homology in the cysteine metal binding motifs between metallothionein proteins isolated from divergent species.

DETAILED DESCRIPTION OF THE INVENTION

Figure 1:
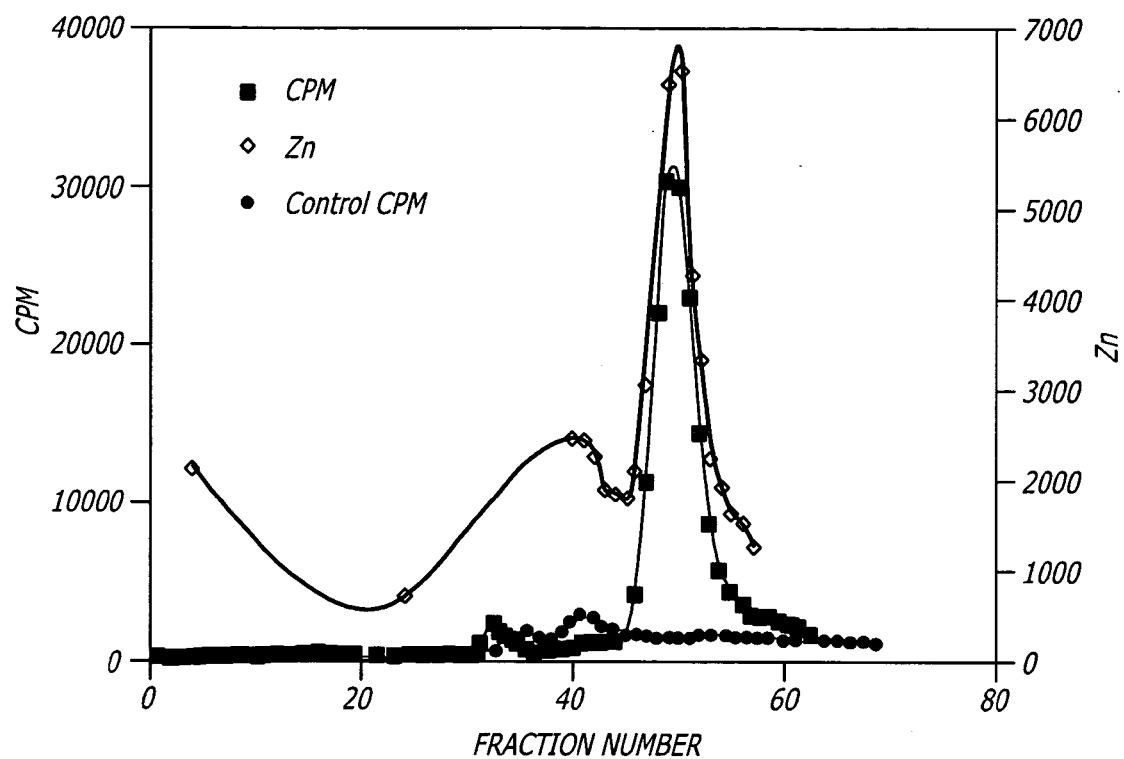
FIG. 1 is an elution profile of exemplary metal binding proteins of the present invention illustrating co-elution of metal binding proteins with the heavy metal zinc.

Metal binding proteins such as metallothioneins (MTs) that have been isolated from various species such as humans, mice, bacteria species, crabs, fish, yeast and chickens, are known to have very similar structural characteristics such as similar size (about 6.0-6.8 kDa), high amino acid sequence conservation, and a high percentage of cysteine residues in the proteins' total amino acid compositions. It is the cysteine composition of these MTs that accounts for the protein's binding affinity for heavy metals including, but not limited to, arsenic, zinc, copper, cadmium, mercury, cobalt, lead, nickel, chromium, uranium, platinum, silver and gold. Unless otherwise stated, the term protein refers to proteins, polypeptides and peptides. The metal binding proteins of the present invention also bind heavy metals complexes in which the heavy metals are associated with a protein or other molecule.

For example, the metal binding proteins, and devices comprising them, called regenerative metal binding supports, disclosed herein are useful in connection with the treatment of any substrate having a concentration of at least one metal, such as a heavy metal. As will be appreciated by those skilled in the art, such heavy metal containing substrates can be any environmental or industrial material such as ground water, drinking water, contaminated soil, waste, or the like, containing a concentration of metal. Similarly, the methods of the present invention are equally useful in treating industrial or municipal wastes containing metals that are desirable to remove. This broad utility makes the compositions and associated methods of the present invention particularly useful in a wide variety of circumstances.

The metal binding proteins and regenerative metal binding supports of the present invention are useful in the recovery of metals, particularly precious metals from metal-containing substrates. For example, the metal binding proteins of the present invention can be used in metal mining processes for the isolation and removal of precious metals such as gold, platinum and silver. Doing so eliminates the need to use other toxic materials such as cyanide in the final stages of metal purification from ore. These same novel techniques can be utilized to recover such metals from industrial or municipal waste. With the ever-increasing use of disposable and other electronic devices, such waste sources are increasingly full of such metals, making recovery a worthwhile endeavor.

The metal binding proteins of the present invention can be isolated easily and efficiently from natural sources or synthetically produced as disclosed herein for use in metal recovery, metal mining, metal recycling, metal remediation, pollution control or any process including metal sequestering. Therefore, the metal binding proteins and associated methods of the present invention provide a versatile, easily produced, efficient and reliable resource for use in any process having a metal binding aspect.

In one embodiment of the present invention, metal binding proteins were isolated from brine shrimp (*Artemia*). *Artemia* MT are a family of metal binding proteins that are referred to as "isomers". Analysis of these proteins' unique amino acid compositions showed each isoform to be essentially equivalent. At least five individual *Artemia* MT isoforms have been identified in accordance with the teachings of the present invention. Unlike MTs from other organisms which share a high degree of sequence homology or similarity, the *Artemia* metal binding proteins have unexpectedly different structural characteristics but possess a high degree of sequence homology to one another.

The following techniques were utilized to provide nucleic acid sequence encoding a *Artemia* metal binding protein. First, metal binding proteins from brine shrimp (*Artemia*) were isolated and purified. N-terminal amino acid sequence analysis was performed on the isolated metal binding protein. Amino acid sequence analysis indicated that the metal binding motif of the first six cysteine residues of the *Artemia* metal binding protein was conserved when compared to rabbit and human MTs, indicating the importance of these amino acid residues in the protein's metal binding function (Hamer D H, Metallothionein. Ann. Rev. Biochem. 55:813-51, 1986). This conservation of the cysteine-rich metal binding motif is seen across a wide variety of divergent species (FIG. 8).

Using this N-terminal amino acid sequence information, oligonucleotide primers corresponding to the N-terminal amino acid sequence were constructed as known in the art. These oligonucleotide primers were used to amplify, by polymerase chain reaction (PCR) potential candidates for a MT gene sequence encoding at least one of the target metal binding proteins from brine shrimp (*Artemia*). The PCR product was purified using QiaPrep spin columns (Qiagen, Inc.) and cloned into the TA cloning vector CR2.1 (Invitrogen) using the manufacturer's protocol. Electrocompetent *Escherichia coli* (Sure Shot cells from Invitrogen) were transformed with the recombinant vector and plated onto LB agar plates containing ampicillin (100 µg/ml) and 1% glucose. The plates were placed at 37° C. overnight. Individual colonies were picked and used to inoculate 5 mL of LB broth supplemented with ampicillin and 1% glucose. The cultures were incubated overnight in a rotary incubator at 37° C. Plasmid was isolate from 2 mL of the cell suspension using QiaPrep spin columns as per the manufacturer's protocol (Qiagen). The plasmid was then sequenced on a Li Cor 4200L using the M13 universal forward and reverse primers. Once verified and determined to be a sequence encoding a metal binding protein, the brine shrimp MT gene was subcloned into the bacterial expression vector pTMZ. Based upon the identified MT encoding sequence, the amino acid sequence of the first novel metal binding proteins of the present invention was determined.

FIG. 1 details an exemplary elution profile utilizing an exemplary metal binding protein of the present invention. This profile was obtained utilizing the following exemplary protocol. *E. coli* (Strain ER 2566) were transformed with a plasmid expression vector containing the MT gene sequence of SEQ ID NO. 1 in pTMZ. Bacteria were grown in LB broth containing 1% glucose at 37° C. to an $A_{600}$ of 0.60. The bacterial cells were collected and resuspended in LB broth containing 0.1% glucose and incubated for 45 minutes at the same temperature. Isopropyl b-D-thiogalactopyranoside (IPTG) was added to a final concentration of 0.1 mM. The bacterial cells were incubated for about 16 hours. Non-transformed bacteria were used as controls. The cells were collected by centrifugation and sonicated in 10 mM Tris, pH 8.0, 5 mM dithiothreitol (DTT) and 0.5 mM phenylmethylsulfonylfluoride (PMSF). The homogenate was centrifuged at 150,000×g for 1 hour at 4° C. The supernatant was collected and incubated with 2 µCi of $^{109}$Cd at room temperature. The radiolabeled supernatant was then applied to a G-50 molecular exclusion column and eluted with 50 mM Tris, pH 8.0. Five milliliter fractions were collected and assayed for radioactivity (CPM) and zinc (Zn), the zinc being an endogenous metal that associates with the exogenous metal binding protein expressed by the transformed bacteria. Each fraction eluting from the column was assayed for Zn by ICPMS (Inductively Coupled Plasma Mass Spectroscopy). Other nucleotide sequence that encode a functional metal binding protein, including, but not limited to SEQ ID NO. 3, may also be utilized, as provided and disclosed by the teachings of the present invention.

Therefore, the present invention provides substantially purified metal binding proteins for use in removal of metals from metal-containing substrates by reversibly binding the metal to the metal binding proteins immobilized on a solid support. The term "substantially purified", as used herein, refers to nucleic acids, amino acids or proteins that have been removed from their natural environment, isolated or separated and are at least 60% free, preferably 75% free, to 90% or more free from other components with which they are naturally associated.

A substantially purified metal binding protein in accordance with the teachings of the present invention has an amino acid sequence analogous to:

SEQ ID NO.2

```
MET ASP CYS CYS LYS ASN GLY CYS THR CYS ALA PRO ASN CYS LYS 15

CYS ALA LYS ASP CYS LYS CYS CYS LYS GLY CYS GLU CYS LYS SER 30

ASN PRO GLU CYS LYS CYS GLU LYS ASN CYS SER CYS ASN SER CYS 45

GLY CYS HIS 48
```

Also within the scope of the present invention are substantially purified metal binding proteins that are variants of the sequence of the above SEQ ID NO. 2 that preserve the protein's metal binding affinity. In particular, conservative amino acid substitutions within the scope of the present can include any of the following: (1) any substitution of isoleucine for leucine or valine, leucine for isoleucine, and valine for leucine or isoleucine; (2) any substitution of aspartic acid for glutamic acid and of glutamic acid for aspartic acid; (3) any substitution of glutamine for asparagine and of asparagine for glutamine; and (4) any substitution of serine for threonine and of threonine for serine.

A "conservative amino acid substitution" as used herein, refers to alteration of an amino acid sequence by substituting an amino acid having similar structural or chemical properties. Those skilled in the art can determine which amino acid residues may be substituted, inserted or altered without the metal binding properties of the proteins of the present invention.

Other substitutions can also be considered conservative, depending upon the environment of the particular amino acid. For example, glycine and alanine can be interchangeable, as can be alanine and valine. Methionine, which is relatively hydrophobic, can be interchanged frequently with leucine and isoleucine, and sometimes with valine. Lysine and arginine are interchangeable in locations in which the significant feature of the amino acid residue is its charge and the different pKs of these two amino acid residues and where their different sizes are not significant. Still other changes can be considered "conservative" in particular environments, as known in the art.

For example, if an amino acid on the surface of a protein is not involved in a hydrogen bond or salt bridge interaction with another molecule, such as another protein subunit or a ligand bound by the protein, negatively charged amino acids such as glutamic acid and aspartic acid can be substituted with positively charged amino acids such as lysine or arginine and vice versa. Histidine, which is more weakly basic than arginine or lysine, and is partially charged at neutral pH, can sometimes be substituted for these more basic amino acids as well. Additionally, the amides glutamine and asparagine can sometimes be substituted for their carboxylic acid homologues, glutamic acid and aspartic acid.

The *Artemia* metal binding proteins of the present invention, and their associated methods of production and use, are a family of metal binding proteins having multiple isomeric forms. As a result, the present invention includes at least five isomeric forms of *Artemia* metal binding proteins suitable for use in removal or recovery of heavy metals. An isomer is one of two or more compounds that have the same chemical composition but differ in structural form. The "isomers" of the present invention have the requisite structural features that classify them as metal binding proteins. These features include their high cysteine content, which confers their metal binding capacity. The isomers differ by two or more amino acid residues, resulting in different pI's for the individual isomer. This pI difference allows easy separation and characterization of the isoforms. Therefore, the metal binding proteins of the present invention can be expressed and produced efficiently and with ease.

In addition to their metal binding properties, these metal binding proteins also exhibit features which render them particularly useful in a wide variety of metal recovery and metal remediation settings. For example, these metal binding proteins are capable of heavy metal binding under a range of conditions such as under moderate to high temperature conditions. The metal binding proteins are capable of heavy metal binding at room temperature and therefore particularly ideal for many applications. The metal binding proteins are also capable of heavy metal binding within a wide temperature range such as, for example, a temperature range of about 4° C. to about 100° C. Those skilled in the art will appreciate that depending on a particular application or operation in which the metal binding proteins are to be utilized, a particular temperature range may be preferred for practical or economic reasons. For example, it may be more practical to use the metal binding proteins "on-site" or at the location of an environmental contamination (which would dictate that particular temperature range that can be obtained within available costs). On the other hand, more effective metal extraction on certain substrates may be achieved by use of the metal binding proteins of the present invention under relatively high temperature conditions. Therefore, in accordance with the teachings of the present invention, a suitable range of temperatures for practicing the present invention includes a range of about 4° C. to about 100° C. This range of temperature conditions makes the metal binding proteins of the present invention more versatile and useful.

In further accordance with the teachings of the present invention, the metal binding proteins can be utilized as a naked composition or in association with a support or dispersal means to aid in either the dispersal, handling, packaging or function of the metal binding protein in metal recovery, metal remediation or metal binding processes. Such metal binding proteins are particularly useful in metal recovery, metal remediation and metal binding processes because they can be more easily and safely used as compared to other methodologies, such as chemical extraction, which exposes the user to toxic or other potentially dangerous types of chemicals.

A variety of solid supports to aid in the handling or dispersal of the novel metal binding proteins can be used and include a hydrophilic membrane, partially hydrophilic membrane, composite membrane, porous organic solid support, nonporous organic solid support, porous inorganic solid support, nonporous inorganic solid supports and combinations thereof. If the solid support is a membrane, membranes such as those described in U.S. Pat. Nos. 5,618,433 and 5,547,760, both of which are herein incorporated by reference in their entirety, are exemplary. If the solid support is an inorganic or organic particulate solid support, preferred solid supports include sand, silicas, silicates, silica gel, glass, glass beads, glass fibers, alumina, zirconia, titania, nickel oxide polyacrylate, polystyrene, polyphenol and others as described in U.S. Pat. Nos. 4,943,375, 4,952,321, 4,959,153, 4,960,882, 5,039,419, 5,071,819, 5,078,978, 5,084,430, 5,173,470, 5,179,213, 5,182,251, 5,190,661, 5,244,856, 5,273,660 and 5,393,892 which are herein incorporated by reference. Specific examples include flexible membranes, beads or particulates, filters, or any other solid supports known in the art that are useful for separations.

In one illustrative embodiment, the solid support is in the form of a membrane. Preferably, the membrane is a polymer, and more preferably is a member selected from the group consisting of fluorinated polymers, polyolefins, polystyrene, substituted polystyrenes, polysulfones, polyesters, polyacrylates, polycarbonates; vinyl polymers, copolymers of butadiene and styrene, fluorinated ethylene-propylene copolymers, ethylenechlorotrifluoroethylene copolymers, nylon and mixtures thereof.

The metal binding proteins of the present invention are associated with a support, such as a polymer membrane, by covalent bonding of the metal binding protein to the polymer to by non-covalent binding such as, but not limited to, electrostatic attractions, dispersion forces and solvent-mediated forces.

In one embodiment of the present invention, at least one metal binding protein is associated with a solid support such that a regenerative metal binding support is provided, wherein the regenerative metal binding support can bind heavy metals from a substrate, the heavy metals can be released from the regenerative metal binding support and the regenerative metal binding support can be reused to bind heavy metalss.

isolation process comprises: (1) preparation of one or more sample(s) containing nucleic acids from brine shrimp (*Artemia*); (2) isolation of total RNA from *Artemia*; (3) preparation of cDNA from the total RNA; (4) amplification of metal binding protein gene sequences; and (5) cloning, sequencing and verification of an isolated nucleic acid sequence as a metal binding protein gene (MT) from brine shrimp (*Artemia*).

The above procedure yielded the entire coding sequence for one of the metal binding protein genes, metallothionein (MT). This sequence is:

SEQ ID NO.1

```
5'-ATG GAC TGC TGC AAG AAC GGT TGC ACC TGT GCC CCA AAT TGC AAA  45
   TGT GCC AAA GAC TGC AAA TGC TGC AAA GGT TGT GAG TGC AAA AGC  90
   AAC CCA GAA TGC AAA TGT GAG AAG AAC TGT TCA TGC AAC TCA TGT 135
   GGT TGT CAC TGA-3' 147
```

In general, a substrate from which one or more heavy metal species are to be removed is contacted with a metal binding protein bound to a solid support, where the metal binding protein has an affinity for the heavy metal. The solid support forms a support for the metal binding protein and can be in the form of a membrane, beads or solid support particulates, or any other form commonly used in biochemical or chemical separations. If a membrane is used as the solid support, the metal binding protein—solid support composition can be incorporated into a contacting device comprising a housing, e.g., cartridge, containing the composition of matter of the invention by causing solution containing desired ions to flow through the cartridge and thus come in contact with the composition of the invention. In one embodiment, the membrane configuration is a pleated membrane, although other membrane configurations, such as flat sheet, stacked disk or hollow fibers may be used. However, various contact apparatus may be used instead of a cartridge such as but not limited to a cassette, syringe, unit, canister, multi-well plate or filter holder. If a solid support is used, separation columns can be used as are known in the art.

It should be noted, that an additional characteristic feature of the metal binding proteins are that they are also capable of reversible heavy metal binding. For example, bound metals can be eluted off or away from the metal binding proteins using acidic conditions or by instantaneous exchange reactions or inorganic chelators. For example, during incubation of a metal binding protein with radioactive Cd, the $^{109}$Cd metal exchanges for endogenous metal bound to the metal binding protein. At about pH 1.0, the metal is released from the protein. Bringing the pH of the solution up to about pH 8.0 regenerates the metal binding activity of the protein. Therefore, due to the reversible binding characteristics of the novel metal binding proteins, the present invention also provides compositions, formulations, powders, liquids, devices or apparatuses comprising the substantially purified metal binding proteins which can be utilized more than once.

Turning now to an exemplary discussion of the genetic engineering of the novel metal binding proteins of the present invention, a nucleotide sequence for one of the isoforms of a metal binding protein from a brine shrimp (*Artemia*) was identified, as discussed above. Generally, the Species as divergent as humans and wheat express metallothionein proteins with similar binding affinities for heavy metals. These MT proteins contain from 12 to 22 cysteine residues, which are conserved across divergent species. These cysteine residues form metal binding motifs responsible for the metal binding function of the proteins (Hamer D H, Metallothionein. Ann. Rev. Biochem. 55:813-51, 1986). Therefore, one embodiment of the present invention provides MT proteins immobilized on solid supports, such as membranes, wherein the MT are isolated from organisms including, but not limited to, mammals, fish, mollusks, echinoderms, crustaceans, reptiles, nematodes, grains and yeast. Non-limiting examples of these organisms include, but are not limited to, brine shrimp (*Artemia*), rabbit (*Oryctolagus cuniculus*), green monkey (*Cercopithecus aethiops*), human (*Homo sapiens*), channel catfish (*Ictalurus punctatus*), African clawed frog (*Xenopus laevis*), blue mussel (*Mytilus edulis*), painted sea urchin (*Lytechinus pictus*), fruit fly (*Drosophila melanogaster*), roundworm (*Caenorhabditis elegans*), rice (*Oryza sativa*), wheat (*Triticum aestivum*) and yeast (*Candida glabrata*).

One embodiment of the present invention provides one or more nucleic acid sequences encoding a substantially purified metal binding protein having amino acid sequence analogous to at least one metallothionein protein from an organism including, but not limited to, *Artemia*, mammals and marine species, or other species having a metallothionein protein with conserved amino acid sequence homology in the cysteine residues, e.g. the metal binding motifs, as compared to *Artemia* MT (FIG. 8).

Another embodiment of the present invention provides one or more amino acid sequences encoding a substantially purified metal binding protein analogous to at least one metallothionein protein from an organism including, but not limited to, *Artemia*, mammals and marine species, or other species having a metallothionein protein with conserved amino acid sequence homology in the cysteine residues, e.g. the metal binding motifs, as compared to *Artemia* MT (FIG. 8). Exemplary amino acid sequences include the sequences of SEQ ID NO. 2 and SEQ ID NOs. 11-23 (FIG. 8).

Alternatively, an isolated nucleic acid can comprise the minimal DNA sequences sufficient to allow translation of a functional metal binding protein. A functional metal binding protein need not be the entire native metal binding protein but can be just those portions or regions of SEQ ID NO. 1 that encodes a protein capable of binding to heavy metals. Therefore, the invention also includes isolated nucleic acids including DNA having at least 80% sequence identity to a DNA molecule having the sequence of nucleotide residues 1 to 66 of SEQ ID NO 1.

Also within the present invention is a nucleic acid sequence encoding any one of the novel metal binding proteins of the present invention. Such novel metal binding proteins can have molecular weight of about 5,800 daltons and are able to bind with high affinity to heavy metal ions such as arsenic, zinc, copper, cadmium, mercury, cobalt, lead, nickel, platinum, silver and gold. The novel metal binding proteins include therein an amino acid sequence selected from the group consisting of: SEQ ID NO: 2 and sequences incorporating one or more conservative amino acid substitutions thereof wherein the conservative amino acid substitutions are any of the following: (1) any of isoleucine, leucine and valine for any other of these amino acids; (2) aspartic acid for glutamic acid and vice versa; (3) glutamine for asparagine and vice versa; and (4) serine for threonine and vice versa. Alternative nucleic acid sequences can be determined using the standard genetic code; the alternative codons are readily determinable for each amino acid in this sequence.

It should be noted, that while the isolated nucleic acids provided herein can be used to produce or express novel metal binding proteins, they are also particularly useful for isolation and identification of additional metal binding protein genes encoding the novel metal binding proteins of the present invention. For example, using the strategy, exemplary methods and nucleic acid sequences provided herein, DNA sequences encoding any of the metal binding protein isomers can be obtained. Therefore, the present invention includes nucleic acids encoding any and all of the isomeric or alternative forms of the metal binding proteins of the present invention. Additionally, isolated nucleic acids need not comprise entire coding sequences of an MT isomer, but include nucleic acid sequences encoding domains or portions of a coding sequence encoding an MT isomer, such as the functional or metal binding regions of the metal binding protein isomers of the present invention.

Another aspect of the invention is a vector comprising a nucleic acid sequence according to the present invention operatively linked to at least one control sequence that controls the expression or regulation of the nucleic acid sequence. Such control sequences are well known in the art and include operators, promoters, enhancers, promoter-proximal elements and replication origins. The techniques of vector construction, including cloning, ligation, gap-filling, the use of the polymerase chain reaction (PCR), solid-state oligonucleotide synthesis, and other techniques, are all well known in the art and need not be described further here. The vectors of the present invention are particularly useful in producing the novel metal binding proteins either by modified organisms, host cells or other types of expression systems. The metal binding proteins of the present invention can be produced in bacterial cells, insect cells, plant cells or mammalian cells. Appropriate vectors and cells for production of metal binding proteins in each of these species are well known to persons skilled in the art.

Turning now to uses for the metal binding proteins of the present invention. Exemplary uses of these proteins include pollution control applications such as metal remediation, pollution control, metal recycling or metal mining. For example, the metal binding proteins can be used to reduce the concentration of heavy metals in an environmental substance. The substance can be a fluid, such as ground water, sludge, waste-water and the like. Additionally, the metal binding proteins can be incorporated into one or more compositions or devices used for pollution control. For example, the metal binding proteins can be applied on site in the form of a flocculent or powder, or can be used in treatment plants as part of a membrane filtration or other type of solid support device used for removal of heavy metal from a contaminated substrate.

The metal binding proteins used in these metal binding processes can be provided as a product purified from its natural source or can be produced by bioengineering techniques. For example, the metal binding proteins can be produced by transgenic or modified organisms. Modified organisms include transgenic animals, bacteria or plants. For example, a modified plant can be a transgenic tobacco plant whose genome has been genetically altered to express one or more metal binding protein of the present invention. A modified organism can also include a plant or biomass that is capable of growing at or within contaminated sites where metal remediation is desired. Extraction of metal contaminants by the modified organisms also concentrates the toxic metals from the contaminated site. This provides the additional advantage of converting the heavy metals to a smaller quantity as well as providing final product that is more easily and safely handled for disposal or further processing.

Methods for reducing the concentration of heavy metals in a substrate include contacting a metal binding protein of the present invention with a substrate having heavy metals. In a non-limiting example, a metal binding protein having an amino acid sequence analogous to at least one metal binding protein sequence from brine shrimp (*Artemia*) can be contacted with a substance having a concentration of at least one heavy metal to bind the heavy metal to the metal binding protein. Subsequently, the bound heavy metal can be separated from the substrate, reducing the concentration of heavy metals in the original substrate.

As mentioned previously, an additional advantageous feature of the metal binding proteins of the present invention include their ability to release bound heavy metals using acid extraction, inorganic chelators, and/or exchange reaction technologies. This allows the user, if desired, to elute bound heavy metals off the metal binding proteins. Once the heavy metals are eluted off the metal binding proteins of the present invention, the metal binding proteins can be regenerated (or recycled) for additional uses in metal extraction. Therefore, the invention also provides methods for reducing the concentration of heavy metals in a substrate using reusable compositions, devices and apparatuses comprising the metal binding proteins.

Metal binding proteins of the present invention, when used in methods for reducing the concentration of a metal in a substrate can be provided in such a way as is appropriate for the particular use, situation, mode of administration or environment in which the metal binding proteins are to be used. For example, when used in metal remediation, or in pollution control, the metal binding proteins can be coupled to a support, such as a powder and used, for example, as a flocculent to provide a convenient and efficient means of dispersing the metal binding proteins.

Alternatively, the metal binding proteins can be provided coupled to a membrane, a semi-permeable membrane, a filter, or any other means appropriate for allowing sufficient exposure of the metal binding proteins to the heavy metal containing substrate so as to bind or sequester the heavy metals from the substrate. A membrane or filter comprising the metal binding proteins provides a particularly efficient means of treating ground water or waste water, as contaminated water can be purified by passage through the membrane or filter without further clean up as is required in chemical extraction processes. Coupling the metal binding proteins to a support or supporting matrix also affords easier handling of the metal binding proteins especially when used in large scale or industrial applications.

Use of the metal binding proteins of the present invention are not limited only to those methods where removal of heavy metals is desired, but can also include methods where recovery or concentration of heavy metals in a substance is to be achieved. For example, the metal binding proteins can be used for metal mining, such as in the recovery of precious metals including gold, platinum and silver, or can be used to concentrate metals in hazardous conditions, such as hazardous waste containing radioactive metals. Such hazardous metal waste can result either from numerous research, commercial or industrial uses.

Use of the metal binding proteins in concentrating radioactive metals from waste also reduces the amount or quantity of hazardous waste to be disposed of. Reducing the quantity of hazardous metal waste also reduces the level of radioactivity to which certain individuals are exposed.

Methods for reducing the concentration of heavy metals in a substance include producing the metal binding proteins in a modified organism. Modified organisms include, for example, transgenic organisms or transgenic hosts. For example, hosts or organisms such as shrimp, plants, bacteria, yeast or algae can be modified using molecular and genetic engineering techniques well known in the art. Using these techniques, which are described for example, in Sambrook et al., Molecular Cloning: A Laboratory Manual (New York: Cold Spring Harbor Press, 2001); Ausubel et al. Current Protocols in Molecular Biology (Wiley Interscience Publishers, 1995); US Dept Commerce/NOAA/NMFS/NWFSC Molecular Biology Protocols (URL: http://research.nwfsc.noaa.gov/protocols.html); or Protocols Online (URL:www.protocol-online.net/molbio/index.htm), organisms whose genomes are modified so as to result in expression of a metal binding protein are provided. Metal binding proteins of the present invention include metal binding proteins having an amino acid sequence analogous to at least one metal binding protein sequence from a brine shrimp (Artemia). Modified organisms can be made and used to produce these metal binding proteins, and the metal binding proteins useful in the methods provided herein.

A modified organism producing a metal binding protein of the present invention includes a modified organism producing at least one metal binding protein having an amino acid sequence substantially similar to a metal binding protein from a brine shrimp (Artemia). A modified organism also includes an organism producing a metal binding protein having an amino acid sequence substantially similar to SEQ ID NO. 2 or conservative amino acid substitutions thereof.

Alternatively, production or expression of the metal binding proteins of the present invention from modified organisms is not limited to genomic expression of the metal binding proteins, but also includes epigenetic expression of the metal binding proteins from the modified organisms. Methods and techniques for obtaining epigenetic expression from a modified organism include, for example, adenoviral, adeno-associated viral, plasmid and transient expression techniques which are known in the art.

The present invention includes methods for producing the metal binding proteins of the present invention. For example, a method for producing a metal binding protein having an amino acid sequence analogous to at least one metal binding protein from a brine shrimp (Artemia) includes providing an expression system, producing a metal binding protein using the expression system and purifying or isolating the metal binding proteins to obtain a metal binding protein of the present invention.

Expression systems can be systems such as traditional manufacturing plants. For example, organisms such as brine shrimp can be grown and the metal binding proteins of the present invention purified or extracted from the tissues of the brine shrimp. Alternatively, biomanufacturing systems using genetically engineered organisms (produced as described herein) capable of producing the metal binding proteins can be used to produce the metal binding proteins. For example, bacteria containing a metal binding protein expression vector can be cultured on large or small scale (depending on the particular need). The metal binding proteins can then be purified from the bacterial broth and used in metal binding processes.

Therefore, a metal binding protein of the present invention can be produced by expression of a nucleic acid sequence encoding a metal binding protein in a modified organism or host cell. Such a nucleic acid sequence includes, for example, a MT gene such as SEQ ID NO. 1 or a sequence encoding a fragment or functional metal binding domain of a MT gene.

The expressed metal binding proteins are purified using standard techniques. Techniques for purification of cloned proteins are well known in the art and need not be detailed further here. One particularly suitable method of purification is affinity chromatography employing an immobilized antibody to a metal binding protein. Other protein purification methods include chromatography on ion-exchange resins, gel electrophoresis, isoelectric focusing, and gel filtration, among others. Alternatively, the metal binding proteins of the present invention can be purified following their expression from modified organisms by methods such as precipitation with reagents (e.g. ammonium sulfate, acetone or protamine sulfate as well as other methods known in the art).

A further understanding of the present invention will be accorded to those skilled in the art from a consideration of the following non-limiting Examples.

It is emphasized that these examples are illustrative of the principles and teachings of the present invention and are not intended to limit the scope of the invention to exemplary brine shrimp (Artemia) metal binding proteins alone.

EXAMPLE 1

In accordance to the teachings of the present invention, the following exemplary protocols illustrate methods useful in the production, purification and analysis of the metal binding proteins of the present invention.

Sample Preparation

As a preliminary step in the isolation of the metal binding proteins, Artemia brine shrimp were grown in artificial seawater (AS) (422.7 mM NaCl, 7.24 mM KCL, 22.58 mM $MgCl_2.6H_2O$, 25.52 mM $MgSO_4.7H_2O$, 1.33 mM $CaCl_2.2H_2O$ and 0.476 mM $NaHCO_3$). Artemia cysts (2.5 g) were incubated for 48 hours in 250 mL of AS supplemented with antibiotics at 30° C. and rotation at 125 rpm. After 24 hrs, phototropic Artemia were collected, cultured for an additional 24 hrs and then collected by cloth filtration. The shrimp were weighed and if not used immediately, stored at −80° C.

The Artemia were then homogenized in homogenization buffer (HB) (10 mM Tris-HCl (pH 8.0), 0.1 mM DTT, 0.5 mM PMSF and 10 µg/ml Soybean Trypsin Inhibitor) and resuspended in HB at 4 mL/gm wet weight of shrimp. The homogenate was passed through a Yamato LH-21 homogenizer three times at a setting of 800 rpm, filtered through Miracloth (Calbiochem) and the filtrate centrifuged in a Sorvall SA-600 rotor at 14,300 rpm, 4° C. for 30 min. The lipid layer on top of the supernatant was removed by vacuum aspiration and the lower supernatant layer collected and centrifuged in a Beckman 50.2TI rotor at 40K rpm, 4° C. for 90 min. Again, the upper lipid layer was removed and the lower supernatant recentrifuged at 150K (150K sup). The 150K sup was then used immediately or stored at −80° C. If used immediately, this product was then subjected to gel filtration as follows. The gel filtration studies verified the metal binding proteins' ability to bind to heavy metals.

Gel Filtration Studies

The 150K sup was centrifuged in a Sorvall SA-600 rotor at 8,500 rpm and 4° C. for 30 min. The resulting supernatant was then filtered through a HPLC certified 0.45 micron LC13 acrodisc filter (Gelman Sciences). A 20 mL aliquot of filtered 150K supernatant was incubated at 4° C. for 20 min with 2 µL of $^{109}$Cd (0.066 µCi) to radiolabel the metal binding proteins. The sample was then applied to a Sephadex G-50 molecular weight exclusion column (2.6 cm×94 cm) previously equilibrated with 50 mM Tris-HCl (pH 8.0) saturated with $N_2$. One molar DTT (2 µL) was added to fractions 60-100 prior to sample loading in order to maintain reducing conditions in the fractions containing the low molecular weight metal binding proteins. The column was eluted with 50 mM Tris (pH 8.0) at a flow rate of 20 mL/hr while monitoring the eluate at 280 nm. During the elution period, the buffer reservoir was continually purged with $N_2$. Samples used for amino acid analysis were not radiolabeled.

The $^{109}$Cd content (CPM) of the column fractions was determined with an Auto-Logic gamma counter (ABBOTT Laboratories). Zinc content was measured by Flame or Furnace Atomic Absorption Spectroscopy and expressed as PPB zinc/fraction. Prior studies indicated that two classes of metal binding proteins were present, one class being a high molecular weight fraction. However, the majority of $^{109}$Cd eluted with a low molecular weight class of zinc-containing metal binding protein. As shown in FIG. 1, radioactive metal binding protein had a elution peak corresponding to that for Zinc (roughly, fraction #50). The protein concentration of the Sephadex G-50 fractions was determined with a BCA Total protein assay kit (Pierce) according to manufacturers protocol. The distinct structural features of the metal binding proteins of the present invention were then identified in the following studies.

Metal Binding Protein Characterization Studies

Chromatographic and molecular weight studies were performed to ascertain structural features of the metal binding proteins. All protocols used were as described previously in B. Harpham, "Isolation of Metal Binding Proteins From *Artemia*", Master's Thesis, California State University, Long Beach Library, 1998. Using anion exchange and reverse phase chromatography techniques well known in the art and described, for example, in B. Harpham "Isolation of Metal Binding Proteins From *Artemia*", supra, metal binding proteins from *Artemia* were purified and determined to have molecular weights and amino acid sequence length unexpectedly lower than other known metal binding proteins. Under SDS-PAGE conditions, *Artemia* metal binding proteins have molecular weight of about 5.8 kDa as compared to 6-7 kDa for metal binding proteins from other mammalian species. Protein analysis of *Artemia* metal binding proteins indicate a sequence length of 48 amino acids. The *Artemia* MT amino acid sequence was unexpectedly and significantly shorter in length than other known metal binding proteins, which range in length from 60 to 68 amino acid residues.

EXAMPLE 2

Cloning and Sequencing of a Gene Encoding *Artemia* Metal Binding Protein

Total RNA was isolated from 48 hour nauplii (the larval stage of *Artemia*) using the RNAzol method. Forty-eight hour nauplii samples were prepared as described above in Example 1. The PolyTract Procedure (Promega, Wis.) was then used to isolate mRNA from the total RNA samples. cDNA was generated from the mRNA using SuperScript and 3' RACE Kit procedures (Cat #18373, Gibco/BRL, WI) and then subjected to the following synthesis reaction.

| cDNA synthesis reaction: | |
| --- | --- |
| *Artemia* mRNA | 25 µl (500 ng) |
| DEPC $H_2O$ | 30 µl |
| 10 µM AP | 5 µl |

The above mixture was incubated for 10 min at 70° C., then placed on ice for 1-2 min. Volatilized liquid was collected by centrifugation for 10 sec at 10,000 rpm. The following were then added to the above RNA cocktail to produce a cDNA solution:

| | |
| --- | --- |
| 10× PCR Buffer | 10 µl |
| 25 mM $MgCl_2$ | 10 µl |
| 10 mM dNTP | 5 µl |
| 0.1 mM DTT | 10 µl |

The above resulting cDNA solution was then mixed and incubated at 42° C. for 5 min. Five (5) µL of Superscript II RT was added and the mixture incubated at 42° C. for 50 min for cDNA synthesis. The reverse transcription reaction was terminated by incubating the solution for 15 min at 70° C., 5 µL of RNase was then added and the solution incubated for 20 min at 37° C. The final solution containing *Artemia* cDNA was then stored at −20° C. until used for PCR amplification as described below.

The initial PCR Primer Sequences used were as follows: the 5' primer (N-terminal side) was designated "MT-Not I" (SEQ ID NO. 5) and the 3' primer (C-terminal side) was designated "dT-Spe I" (SEQ ID NO. 6, SEQ ID NO. 7, SEQ ID NO. 8, or SEQ ID NO. 9)

SEQ ID NO.5
5'-ACC TAT GCG GCC GCA AAT GGA CTG CTG CAA GAA C-3'

SEQ ID NO.6
5'-GCA CCA ACT AGT GCC TTT TTT TTT TTT A-3'

SEQ ID NO.7
5'-GCA CCA ACT AGT GCC TTT TTT TTT TTT C-3'

SEQ ID NO.8
5'-GCA CCA ACT AGT GCC TTT TTT TTT TTT G-3'.

The above 5' and 3' primers were then used in the following amplification cocktail.

| PCR Reaction Cocktail: | |
|---|---|
| 10× PCR Buffer | 5 µl |
| 25 mM MgCl$_2$ | 3 µl |
| 10 mM dNTP | 1 µl |
| 10 µM dT-SpeI | 1 µl |
| 10 µM MT-Not I | 1 µl |

To the above PCR Reaction Cocktail, a Gem 50 wax bead was added to the tube and the tube incubated at 80° C. for 2-3 minutes. Upon hardening of the wax at room temperature for 10-15 min, the following were layered on top of the hardened wax:

| Sterile H$_2$O | 36.5 µl |
|---|---|
| Artemia cDNA mixture | 2 µl |
| Taq Polymerase | 0.5 µl |

This final mixture was then subjected to the following PCR amplification program.

PCR Program:

Initial denaturation for 3 min at 95° C., followed by 29 cycles of:

94° C. for 1 min
49° C. for 1 min
72° C. for 1 min
72° C. for 10 min
Hold at 4° C.

Once amplified, the PCR product was verified for successful amplification on a 1.2% agarose gel. The PCR product was then purified for subsequent cloning using Qiagen QIAquick Gel Extraction (Qiagen, Calif.). The following primers which contain modifying restriction sites incorporated into their sequence were used to amplify and subclone the purified PCR product containing brine shrimp Artemia metal binding protein gene sequences.

SEQ ID NO.9
MT Nco I (5' primer containing an Nde I site):
5'-GCT ACA CAT ATG TCC ATG GAC TGC TGC AAG AAC-3'

SEQ ID NO.10
MT Sal I (3' primer containing Sal I site):
5'-ACG AAC GTC GAC GCC TTT TTT TTT TTT TTT A-3'

Using the MT Nco I and MT Sal I primers, with an annealing temperature of 72° C. for 1 min, the Artemia MT nucleotide sequence was amplified and then subsequently subcloned into the pGEM3 vector's Eco RI site. Once subcloned, the cloned metal binding protein gene can then be easily modified or further processed for use in expression, production or other methods requiring use of an isolated nucleic acid encoding a metal binding protein.

The entire coding sequence for MT gene was then determined using a LiCor 4200L DNA sequencer. Sequence comparison studies of the MT gene from Artemia indicate it to have unexpectedly different sequence as compared to other known metal binding protein genes. When the Artemia MT gene sequence was aligned with that of equine and human MT, homology was observed at the locations of the metal-binding cysteine residues. The ability of the exemplary metal binding protein of the present invention to bind heavy metals was then confirmed in the following studies.

EXAMPLE 3

Transgenic Tobacco Expression of Artemia MT

The following provides an exemplary study which can be performed on any of the novel metal binding proteins of the present invention to aid in the verification of a protein as a metal binding protein. For example, the metal binding proteins of the present invention are capable of binding heavy metals such as zinc, cadmium and copper. The ability of an isolated protein to bind heavy metals was described and detailed in the disclosed transformation of E. coli with an exemplary MT of the present invention and shown, as indicated in FIG. 1.

As described previously, modified organisms useful for producing the novel metal binding proteins of the present invention can be made following the teachings provided herein. An exemplary modified organism includes a transgenic tobacco plant which is particularly useful in the methods described herein.

Figure 2:
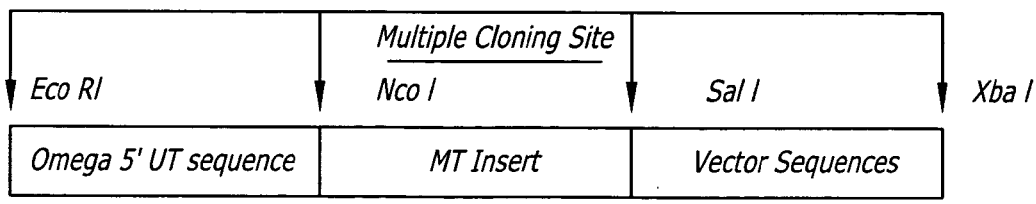
FIG. 2 is a map of an exemplary cloning cassette containing the gene sequence of the metal binding protein gene, in accordance with the teachings of the present invention.
Figure 5:
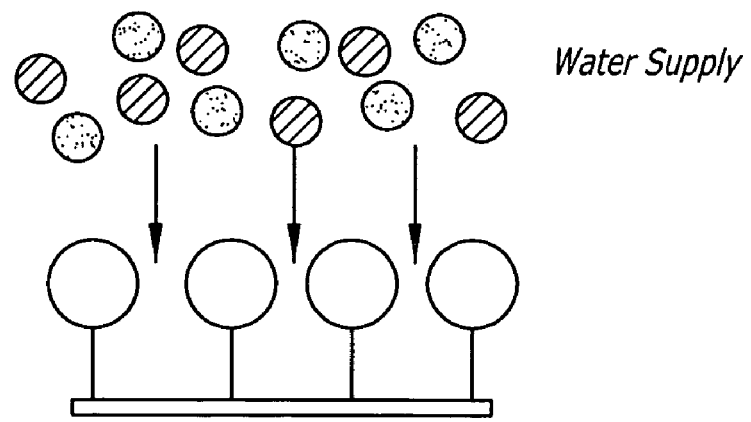
FIG. 5 illustrates the removal of heavy metals from water in accordance with the teachings of the present invention.
Figure 5:
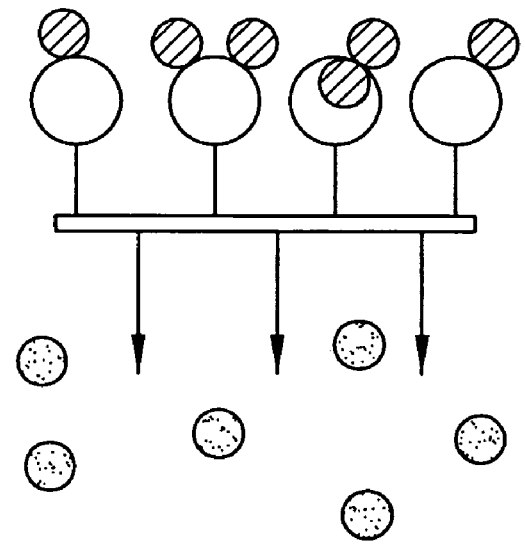
Figure 6:
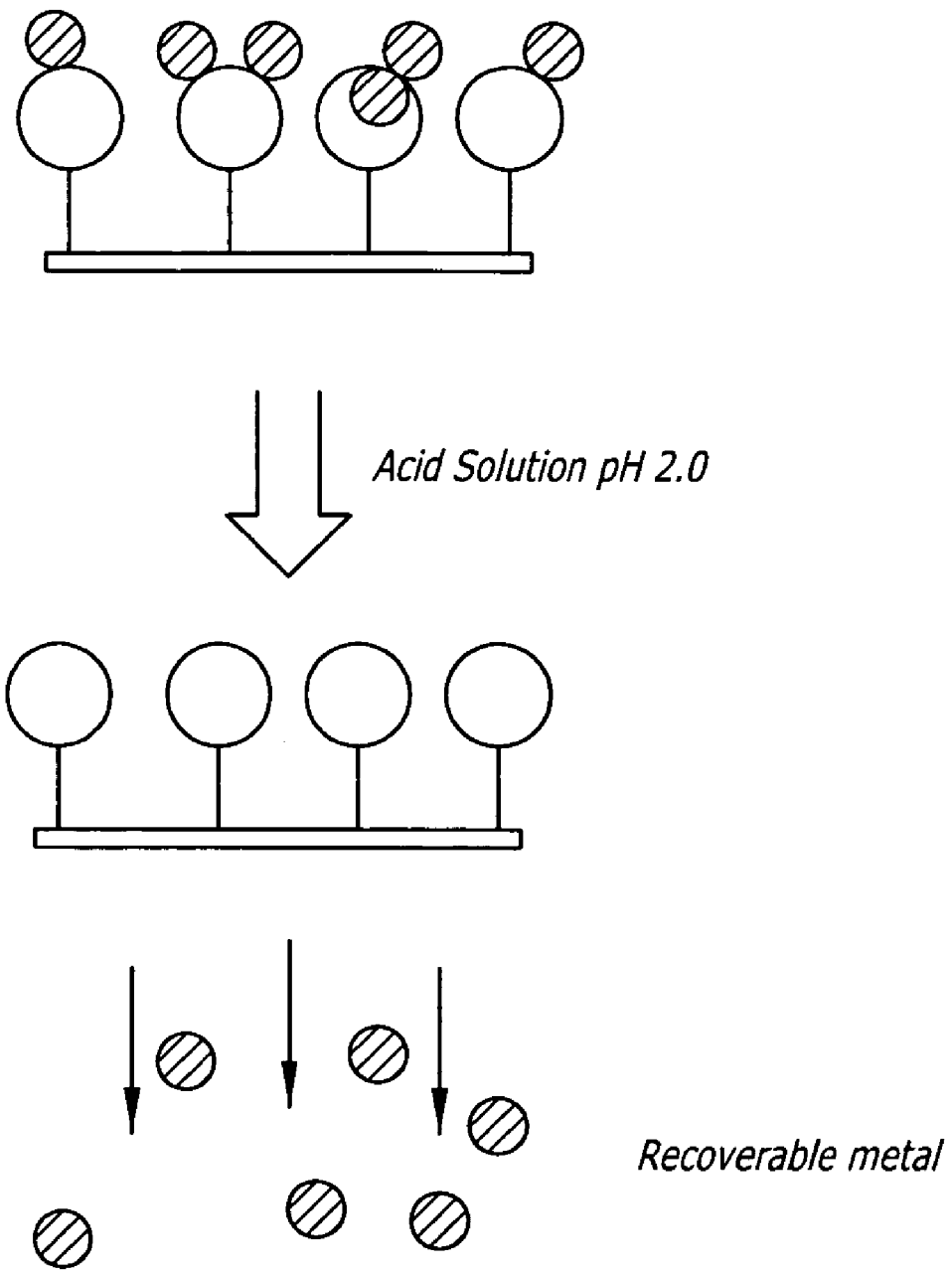
FIG. 6 illustrates the recovery of removed metals from a membrane coated with MT proteins in accordance with the teachings of the present invention.
Figure 7:
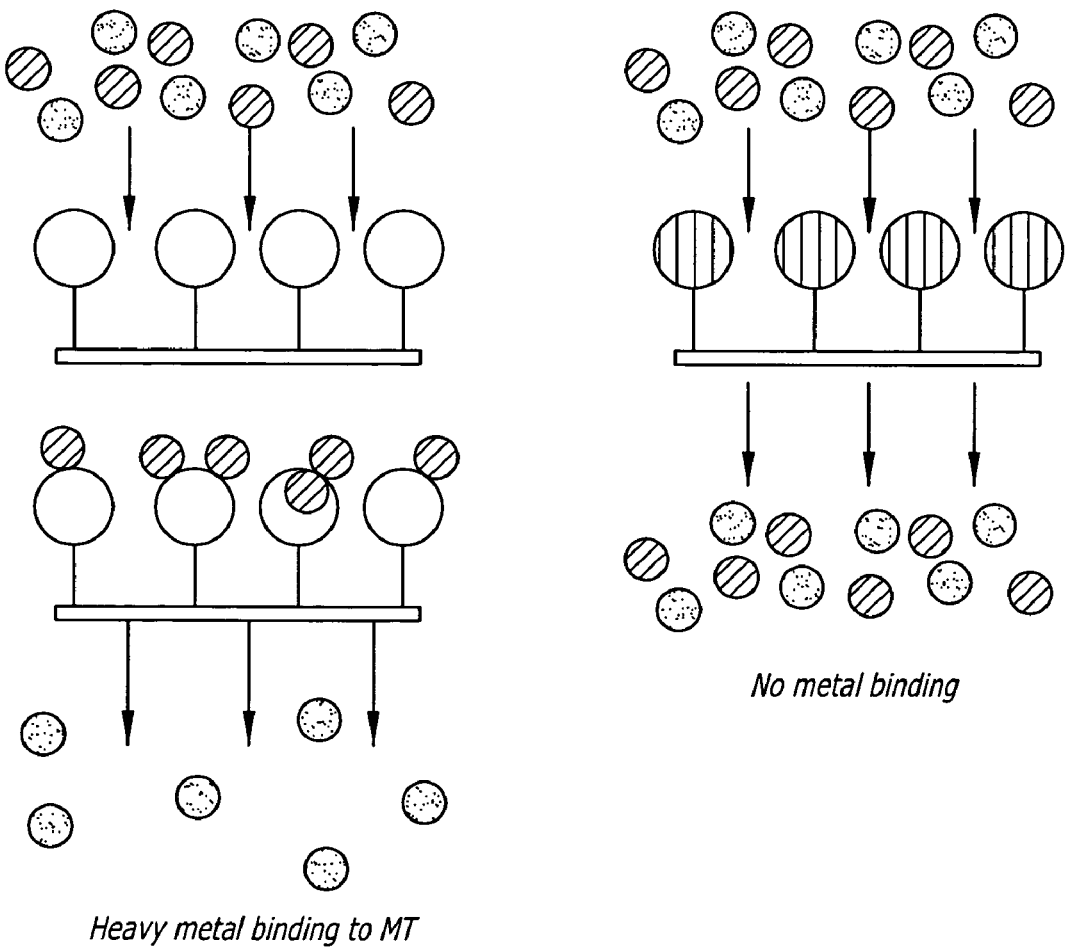
FIG. 7 illustrates the selectivity and affinity of the present invention for binding heavy metals.

The cDNA for MT cloned into TOPO.CR2 vector is referred to as pART$_{mt}$. The coding sequence for the MT was cloned into a pUC18 based plasmid containing the omega 5' untranslated region of the TMV coat protein in frame with the multiple cloning site. (See FIG. 2). This was accomplished by amplification of the MT coding sequence from pART$_{mt}$ using PCR primers containing an Nco I restriction site on the 5' primer and a Sal I site on the 3' primer. The PCR product and vector were each restricted with Nco I and Sal I and purified. The PCR product was then ligated into the vector using T4 DNA ligase. The ligation mixture was used to transform DH5α cells by electroporation. LB media was inoculated with individual colonies and grown overnight. Plasmid was isolated and sequenced to verify the presence and integrity of the MT coding sequence.

The Eco RI/Xba I cassette was removed and cloned into the corresponding sites on the plant expression vector pSS. The pSS vector contains the constitutive CMV promotor and transcription terminator sequence in frame with the multiple cloning site. The resultant pSS$_{mt}$ construct was propagated in DH5α cells, isolated and sequenced to verify the presence and integrity of the MT gene as described above.

MT Expression in Tobacco Leaves

A. tumefaciens were transformed with the cytosolic pSS$_{mt}$ construct by electroporation and grown overnight at 27° C. in YEB medium, pH 7.4, containing antibiotics. The cells were collected and resuspended in induction medium (YEB, pH 5.8, antibiotics and 20 µM Acetosyringone) and grown overnight at 27° C. The next morning the cells were collected by centrifugation and resuspended in infiltration medium (MMA buffer containing antibiotics and 200 µM Acetosyringone) to an A$_{600}$ of 1.5 and incubated at room temperature for 2 hrs. Tobacco (Nicotiana tabacum) leaves were submerged in the bacterial suspension and placed in a vacuum dessicator. The leaves were infiltrated under a vacuum of 30-40 mbar. The leaves were placed at room temperature for 72 hours then ground to a fine powder in liquid nitrogen and extracted with 10 mM Tris pH 8.0, 0.05 mM DTT, 1 mM PMSF. The solution was clarified by centrifugation at 30,000×g and the supernatant assayed for MT using a $^{109}$Cd metal binding assay. Metal binding activity is evident in the leaves containing the gene for Artemia MT (Table 1).

TABLE 1

| Treatment | Bound Cd (CPM) |
| --- | --- |
| Buffer | 747 |
| Untreated Leaves | 5052 |
| Infiltrated Leaves I | 12874 |
| Infiltrated Leaves II | 12763 |

Stable Transformation of Tobacco

A suspension of *A. tumefaciens* transformed with pSS$_{mt}$ were grown as described above. Tobacco leaves were cut into small pieces (without the central vein) and transferred into sterile weck glasses containing 50-100 mL of bacterial suspension (A$_{600}$ about.1.0) and incubated at room temperature for 30 minutes. The leaf pieces were then transferred onto sterile Whatman 3 MM filterpaper pre-wetted with sterile water in plastic petri dishes. The dishes were sealed with saran wrap and incubated at 26-28° C. in the dark for two days. The leaf pieces were then washed with sterile water containing antibiotics and transferred onto MS II agar plates. The pieces were incubated at 25° C. for 3-4 weeks with a 16 hr photoperiod. When shoots began to form, the shoots were removed and transferred onto MS III agar plates and incubated at 25° C. with a 16 hr photoperiod until roots began to form. The small plants were transferred into weck glasses containing MS III medium and incubated at 25° C. with a 16 hr photoperiod for about two weeks. The young plants were then planted into soil. Young leaves from the plants were collected and assayed for MT activity as described above to determine the transgenic plants.

EXAMPLE 4

Polymer Membranes for Toxic Metal Removal from Water

Metallothionein was extracted from *Artemia* embryos as described above. The protein extract (80 mL) was placed in a boiling water bath for 15 minutes. The solution was centrifuged at 30,000×g (16,000 rpm in a SA600 rotor) for 30 minutes at 4° C. The supernatant containing the metallothionein was transferred to a clean tube containing 60 μL of $^{109}$Cd (Amersham Biosciences). The solution was mixed well and allowed to stand at room temperature for five minutes. This allows for exchange of the radioactive cadmium onto the metallothionein and provides us with a method for detecting the protein during its purification. The solution was then applied to a 100×4.8 cm G-50 molecular exclusion column and eluted with nitrogen saturated 50 mM Tris, pH 8.0. Fifteen milliliter fractions were collected into tubes containing 25 μL of 1M DTT. The peak metal binding activity were pooled and stored at 4° C. The solution is referred to as MT. (See FIG. 3 through FIG. 7)

Metal Binding at Neutral pH

Pall Biodyne membranes (Biodyne A and Biodyne B, 0.45 μm, Lot numbers 002245 and 035241, respectively) were used as a solid support for these experiments. A 1 cm$^2$ piece of membrane was placed in a 10 ml Millipore glass frit filtering unit. Ten milliliters of MT was passed through the membrane under vacuum at a flow rate of approximately 100 mL/minute (See FIG. 4). The flow through was collected for protein analysis. Next, 10 mL of a solution of cadmium (0.1 μg/mL of CdCl$_2$ and 10 μL $^{109}$Cd in 50 mL of water) was passed through the membrane under vacuum (See FIG. 5). The membrane was then washed twice, each with 10 mL of PBS. Five milliliters of the pooled eluate was analyzed of radioactivity. The membrane was removed from the filtering unit, place in a 12×75 mm centrifuge tube and analyzed for radioactivity in an LKB gamma counter. As a control, the procedure was repeated with a second membrane that had not been treated with MT. This membrane is referred to as the "blank." The results are shown below in Table 2.

TABLE 2

| Sample | MT Membrane | Blank |
| --- | --- | --- |
| Biodyne A | 152,876 | 3768 |
| Biodyne B | 158,762 | 1774 |

The results demonstrate that membrane-bound MT is capable of removing cadmium(as $^{109}$Cd) from a solution of the metal passed through the membrane. Membranes without MT remove little, if any, metal from the solution.

Metal Binding at Varying pH

The next series of experiments were to determine the effect of extremes of pH on the metal binding activity of the protein on the membrane. A fresh sample of MT was prepared for these studies. The solution of cadmium used for these experiments was prepared as follows: 2 μL of $^{109}$Cd was added to 1 mL of an aqueous solution of CdCl$_2$ (1 ppm). Then 100 μL of this radioactive cadmium solution was added to 10 mL of each of the following solution: PBS, 10 mM glycine, 150 mM NaCl, pH 3.0., and 10 mM H$_2$CO$_3$/HCO$_3$, 150 mM NaCl, pH 10.1. Only the Biodyne A membrane was used for this study. Membranes not treated with MT washed with PBS containing radioactive cadmium served as the controls. Membranes were placed in the Millipore filtering unit and processed as follows:

Membrane #1 (blank) was washed with 5 mL of PBS containing radioactive cadmium. The membrane was then washed twice with 10 mL of non-radioactive, metal-free PBS.

Membrane #2 was washed first with 10 mL of MT solution and then 5 mL of PBS containing radioactive cadmium. The membrane was then washed twice with 10 mL of non-radioactive, metal-free PBS.

Membrane #3 was washed with 10 mL of MT solution and then 5 mL of 10 mM H$_2$CO$_3$/HCO$_3$, 150 mM NaCl, pH 10.1, containing radioactive cadmium. The membrane was then washed twice with 10 mL of non-radioactive, metal-free 10 mM H$_2$CO$_3$/HCO$_3$, 150 mM NaCl, pH 10.1.

Membrane #4 was washed with 10 mL of MT solution and then 5 mL of 10 mM glycine, 150 mM NaCl, pH 2.0, containing radioactive cadmium. The membrane was then washed twice with 10 mL of non-radioactive, metal-free 10 mM glycine, 150 mM NaCl, pH 2.0.

Each membrane was analyzed for radioactivity as described above, The results are shown below in Table 3.

TABLE 3

| Sample | CPM |
| --- | --- |
| Membrane 1 (blank) | 174 |
| Membrane 2 pH 7.5 | 33380 |
| Membrane 3 pH 10.1 | 6890 |
| Membrane 4 pH 2.0 | 651 |

This experiment demonstrates that the membrane-bound MT is capable of binding metal at pHs ranging from 7.5 to 10.1 but does not occur at a pH of 2. Once metal is bound to the MT, it can be recovered by exposing the membrane to acid (pH=2) (See FIG. 6). These experiments were conducted by adding all the solutions directly to the membrane. To evaluate effects of pre-equilibrating the membranes with buffer prior to addition of MT, i.e., is the efficiency of metal binding effected, membranes (Biodyne B) were processed as follows:

Membrane #1 (blank) was washed with 5 mL of PBS containing radioactive cadmium. The membrane was then washed twice with 10 mL of non-radioactive, metal-free PBS.

Membrane #2 was washed first with 10 mL of MT solution and then 5 mL of PBS containing radioactive cadmium. The membrane was then washed twice with 10 mL of non-radioactive, metal-free PBS.

Membrane #3 was pre-washed with 10 mL of metal-free 10 mM $H_2CO_3/HCO_3$, 150 mM NaCl, pH 10.1, then washed with 10 mL of MT solution and then 5 mL of 10 mM $H_2CO_3/HCO_3$, 150 mM NaCl, pH 10.1, containing radioactive cadmium. Finally, the membrane was washed twice with 10 mL of non-radioactive, metal-free 10 mM $H_2CO_3/HCO_3$, 150 mM NaCl, pH 10.1.

The results are shown below in Table 4

TABLE 4

| Sample | CPM |
| --- | --- |
| Membrane #1 | 190 |
| Membrane #2 | 4218 |
| Membrane #3 | 7431 |

Equilibrating the membrane at pH 10.1 results in better efficiency of protein binding to the membrane.

Specificity of MT Metal Binding

Binding affinity/specificity was measured against bovine serum albumin, a protein containing several cysteine residues and known to bind heavy metals. The Biodyne A membrane was used for this experiment. The concentration of MT solution was found to be approximately 7 μg/mL. The concentration of the flow through is equivalent to the starting material indicating that the amount bound to the membrane is in ng (nanograms), thus indicating that the metal binding capacity of the protein is significant. Therefore, 7 μg/mL and 100 μg/mL solutions of BSA were made in D-PBS using the 2 mg/mL BSA standard from Pierce Chemical, Inc. The cadmium binding solution was prepared as follows: 1.5 mL of aqueous 1 ppm $CdCl_2$ was mixed with 3 μL of $^{109}Cd$. The solution is stored at 4° C. The assay was run as follows:

Membrane #1 (blank) was washed with 5 mL of PBS containing radioactive cadmium. The membrane was then washed twice with 10 mL of non-radioactive, metal free PBS.

Membrane #2 was washed first with 5 mL of MT solution and then 5 mL of PBS containing radioactive cadmium. The membrane was then washed twice with 10 mL of non-radioactive, metal free PBS.

Membrane #3 was washed with 5 mL of BSA solution (7 μg/mL) and then 5 mL of PBS containing radioactive cadmium. The membrane was then washed twice with 10 mL of non-radioactive, metal-free PBS.

Membrane #4 was washed with 10 mL of BSA solution (100 μg/mL) and then 5 mL of PBS containing radioactive cadmium. The membrane was then washed twice with 10 mL of non-radioactive, metal-free PBS.

The results of these experiments are shown below in Table 5.

TABLE 5

| Sample | | CPM |
| --- | --- | --- |
| Membrane 1 | No MT | 174 |
| Membrane 2 | MT (5 mL) | 1171 |
| Membrane 3 | BSA (5 mL of 7 μg/mL) | 77 |
| Membrane 4 | BSA (10 mL of 100 μg/mL) | 151* |

*this membrane was tested a different day where the MT binding activity was greater than 3000 CPM.

Under these experimental conditions, BSA does not remove metal from aqueous solutions, even when using a 10-fold higher concentration of BSA than MT to prepare the membrane. This experiment demonstrates the utility of membrane bound MT for remediation of metal from water or other aqueous substrates (see FIG. 7).

Effect of Temperature on Metal Binding Activity.

These binding experiments were performed with Biodyne A membranes.

Membrane #1 (blank) was washed with 5 mL of PBS containing radioactive cadmium. The membrane was then washed twice with 10 mL of non-radioactive, metal-free PBS.

Membrane #2 was washed with 10 mL of MT solution and then 5 mL of PBS containing radioactive cadmium pre-warmed to 60° C. The membrane was then washed twice with 10 mL of non-radioactive, metal-free PBS pre-warmed to 60° C.

Membrane #3 was washed with 10 mL of MT solution and then 5 mL of PBS containing radioactive cadmium cooled to 4° C. The membrane was then washed twice with 10 mL of non-radioactive, metal free PBS cooled to 4° C.

The results of these experiments are shown below in Table 6.

TABLE 6

| Sample | CPM |
| --- | --- |
| Membrane #1 | 139 |
| Membrane #2 | 3886 |
| Membrane #3 | 2672 |

EXAMPLE 5

Comparison of Rabbit and *Artemia* MT

Metal remediation with the metal binding proteins of the present invention can be accomplished using metallothionein proteins from a variety of sources. Rabbit liver MT was obtained as a lyophilized protein (Sigma) and solubilized in 400 μL of 50 mM Tris, pH 8.0, 0.001 M DTT to a final concentration of 2.5 mg/mL (rabbit MT stock solution). *Artemia* MT was purified as described supra in Example 4.

Membranes were prepared having bound *Artemia* MT or rabbit liver MT by passing an MT-containing solution through the membrane, as described supra in Example 4. Three membranes, a blank, a membrane bound with *Artemia* MT and a membrane bound with rabbit liver MT, were then placed in a 13 mm scintered glass filtering unit and 10 mL of a metal binding solution (a stock solution of 9000 cpm of $^{109}Cd/25$ μL of solution diluted to 75 μL/10 mL PBS to form the metal binding solution) was passed through the membrane under vacuum. The membrane was then washed three times in PBS, and the membrane-bound radioactivity was measured in a Packard gamma counter. In a second experiment, a larger quantity of *Artemia* MT was bound to the membrane. The results of these two experiments are found in Tables 7 and 8.

TABLE 7

| Sample | | CPM |
| --- | --- | --- |
| Membrane 1 | Blank | 351 |
| Membrane 2 | *Artemia* (20 mL bound to the membrane | 685 |
| Membrane 3 | Rabbit (25 µL of a 2.5 mg/mL solution | 985 |

TABLE 8

| Sample | | CPM |
| --- | --- | --- |
| Membrane 1 | Blank | 231 |
| Membrane 2 | *Artemia* (25 mL bound to the membrane | 980 |

Membrane-bound metallothionein, regardless of source, provides removal of metals from aqueous solutions. In addition, the metal binding activity is a function of the amount of protein applied to the membrane and increasing the amount of MT protein on the membrane results in increased metal binding activity by the membrane.

In closing it is to be understood that the embodiments of the invention disclosed herein are illustrative of the principals of the invention. Other modifications may be employed which are within the scope of the invention and accordingly, the present invention is not limited to that precisely as shown and described in the present specification.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

I claim:

1. A device for removing heavy metals from a substrate comprising:
 a regenerative metal binding support comprising a polymer membrane having associated therewith and at least one substantially purified metallothionein (MT) protein, or a portion thereof, from an organism selected from the group consisting of mammals, fish, mollusks, echinoderms, crustaceans, reptiles, nematodes, grains and yeast;
 wherein said regenerative metal binding support binds said heavy metals thereby removing said heavy metals from said substrate; and
 said binding of heavy metal to said regenerative metal binding support is reversible and wherein said regenerative metal binding support is reusable.

2. The device according to claim 1 wherein said mammal is a human.

3. The device according to claim 1 wherein said mammal is a monkey.

4. The device according to claim 1 wherein said mammal is a rabbit.

5. The device according to claim 1 wherein said fish is a catfish.

6. The device according to claim 1 wherein said mollusk is mussel.

7. The device according to claim 1 wherein said echinoderm is a sea urchin.

8. The device according to claim 1 wherein said reptile is a frog.

9. The device according to claim 1 wherein said grain is rice.

10. The device according to claim 1 wherein said grain is wheat.

11. The device according to claim 1 wherein said MT protein has an amino acid sequence selected from the group consisting of SEQ ID NO. 11, SEQ ID NO. 12, SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 21 and SEQ ID NO. 23.

12. The device according to claim 1 wherein said polymer membrane is nylon.

13. The device according to claim 1 wherein said substrate is a liquid.

14. The device according to claim 1 wherein said heavy metal is a heavy metal complex.

15. A method for removing metals from a substrate comprising:
 contacting said substrate having heavy metals therein with a regenerative metal binding support comprising a polymer membrane having associated therewith at least one substantially purified metallothionein (MT) protein, or a portion thereof, from an organism selected from the group consisting of mammals, fish, mollusks, echinoderms, crustaceans, reptiles, nematodes, grains and yeast;
 binding said heavy metal to said regenerative metal binding support thereby producing a substrate having less heavy metal contained therein.

16. The method according to claim 15 wherein said polymer membrane is nylon.

17. The method according to claim 15 wherein said heavy metal is a heavy metal complex.

18. The device according to claim 15 wherein said substrate is a liquid.

19. The method according to claim 15 further comprising:
 releasing said bound heavy metal from said regenerative metal binding support; and
 regenerating the metal-binding capacity of said regenerative metal binding support.

* * * * *

SEQUENCE LISTING

<160> NUMBER OF SEQ ID NOS: 23

<210> SEQ ID NO 1

-continued

```
<211> LENGTH: 147
<212> TYPE: DNA
<213> ORGANISM: Artemia sp.

<400> SEQUENCE: 1
atggactgct gcaagaacgg ttgcacctgt gccccaaatt gcaaatgtgc caaagactgc      60
aaatgctgca aggttgtga gtgcaaaagc aacccagaat gcaaatgtga gaagaactgt     120
tcatgcaact catgtggttg tcactga                                         147

<210> SEQ ID NO 2
<211> LENGTH: 48
<212> TYPE: PRT
<213> ORGANISM: Artemia sp.

<400> SEQUENCE: 2

Met Asp Cys Cys Lys Asn Gly Cys Thr Cys Ala Pro Asn Cys Lys Cys
1               5                   10                  15

Ala Lys Asp Cys Lys Cys Lys Gly Cys Glu Cys Lys Ser Asn Pro
            20                  25                  30

Glu Cys Lys Cys Glu Lys Asn Cys Ser Cys Asn Ser Cys Gly Cys His
        35                  40                  45

<210> SEQ ID NO 3
<211> LENGTH: 66
<212> TYPE: DNA
<213> ORGANISM: Artemia sp.

<400> SEQUENCE: 3
atggactgct gcaagaacgg ttgcacctgt gccccaaatt gcaaatgtgc caaagactgc      60
aaatgc                                                                66

<210> SEQ ID NO 4
<211> LENGTH: 22
<212> TYPE: PRT
<213> ORGANISM: Artemia sp.

<400> SEQUENCE: 4

Met Asp Cys Cys Lys Asn Gly Cys Thr Cys Ala Pro Asn Cys Lys Cys
1               5                   10                  15

Ala Lys Asp Cys Lys Cys
            20

<210> SEQ ID NO 5
<211> LENGTH: 34
<212> TYPE: DNA
<213> ORGANISM: Artificial
<220> FEATURE:
<223> OTHER INFORMATION: 5' primer (N-terminal side) designated MT-Not I
      for PCR amplification of Artemia metal binding protein sequences

<400> SEQUENCE: 5
acctatgcgg ccgcaaatgg actgctgcaa gaac                                  34

<210> SEQ ID NO 6
<211> LENGTH: 31
<212> TYPE: DNA
<213> ORGANISM: Artificial
<220> FEATURE:
<223> OTHER INFORMATION: 3' primer (C -terminal side) designated dT-Not
      I for PCR amplification of Artemia metal binding protein sequences

<400> SEQUENCE: 6
```

-continued

```
gcaccaacta gtgcctttt ttttttttt a                               31
```

<210> SEQ ID NO 7
<211> LENGTH: 31
<212> TYPE: DNA
<213> ORGANISM: Artificial
<220> FEATURE:
<223> OTHER INFORMATION: 3' primer (C -terminal side) designated dT-Not
      I for PCR amplification of Artemia metal binding protein sequences

<400> SEQUENCE: 7

```
gcaccaacta gtgcctttt ttttttttt c                               31
```

<210> SEQ ID NO 8
<211> LENGTH: 31
<212> TYPE: DNA
<213> ORGANISM: Artificial
<220> FEATURE:
<223> OTHER INFORMATION: 3' primer (C -terminal side) designated dT-Not
      I for PCR amplification of Artemia metal binding protein sequences

<400> SEQUENCE: 8

```
gcaccaacta gtgcctttt ttttttttt g                               31
```

<210> SEQ ID NO 9
<211> LENGTH: 33
<212> TYPE: DNA
<213> ORGANISM: Artificial
<220> FEATURE:
<223> OTHER INFORMATION: 5' primer containing an Nde I site

<400> SEQUENCE: 9

```
gctacacata tgtccatgga ctgctgcaag aac                           33
```

<210> SEQ ID NO 10
<211> LENGTH: 31
<212> TYPE: DNA
<213> ORGANISM: Artificial
<220> FEATURE:
<223> OTHER INFORMATION: 3' primer containing Sal I site

<400> SEQUENCE: 10

```
acgaacgtcg acgcctttt ttttttttt a                               31
```

<210> SEQ ID NO 11
<211> LENGTH: 48
<212> TYPE: PRT
<213> ORGANISM: Artemia sp.

<400> SEQUENCE: 11

```
Met Asp Cys Cys Lys Asn Gly Cys Thr Cys Ala Pro Asn Cys Lys Cys
1               5                   10                  15

Ala Lys Asp Cys Lys Cys Cys Lys Gly Cys Glu Cys Lys Ser Asn Pro
            20                  25                  30

Glu Cys Lys Cys Glu Lys Asn Cys Ser Cys Asn Ser Cys Gly Cys His
        35                  40                  45
```

<210> SEQ ID NO 12
<211> LENGTH: 61
<212> TYPE: PRT
<213> ORGANISM: Oryctolagus cuniculus

<400> SEQUENCE: 12

```
Met Asp Pro Asn Cys Ser Cys Ala Thr Arg Asp Ser Cys Ala Cys Ala
1               5                   10                  15
```

```
Ser Ser Cys Lys Cys Lys Glu Cys Lys Cys Thr Ser Cys Lys Lys Ser
            20                  25                  30

Cys Cys Ser Cys Cys Pro Ala Gly Cys Thr Lys Cys Ala Gln Gly Cys
            35                  40                  45

Ile Cys Lys Gly Ala Leu Asp Lys Ser Cys Ser Cys Ala
 50                  55                  60

<210> SEQ ID NO 13
<211> LENGTH: 61
<212> TYPE: PRT
<213> ORGANISM: Homo sapiens

<400> SEQUENCE: 13

Met Asp Pro Asn Cys Ser Cys Ala Ala Gly Asp Ser Cys Thr Cys Ala
 1               5                  10                  15

Gly Ser Cys Lys Cys Lys Glu Cys Lys Cys Thr Ser Cys Lys Lys Ser
            20                  25                  30

Cys Cys Ser Cys Cys Pro Val Gly Cys Ala Lys Cys Ala Gln Gly Cys
            35                  40                  45

Ile Cys Lys Gly Ala Ser Asp Lys Cys Ser Cys Ala
 50                  55                  60

<210> SEQ ID NO 14
<211> LENGTH: 61
<212> TYPE: PRT
<213> ORGANISM: Cercopithecus aethiops

<400> SEQUENCE: 14

Met Asp Pro Asn Cys Ser Cys Ala Thr Gly Val Ser Cys Thr Cys Ala
 1               5                  10                  15

Asp Ser Cys Lys Cys Lys Glu Cys Lys Cys Thr Ser Cys Lys Lys Ser
            20                  25                  30

Cys Cys Ser Cys Cys Pro Val Gly Cys Ala Lys Cys Ala Gln Gly Cys
            35                  40                  45

Val Cys Lys Gly Ala Ser Glu Lys Cys Asn Cys Ala
 50                  55                  60

<210> SEQ ID NO 15
<211> LENGTH: 60
<212> TYPE: PRT
<213> ORGANISM: Ictalurus punctatus

<400> SEQUENCE: 15

Met Asp Pro Cys Glu Cys Ser Lys Thr Gly Thr Cys Asn Cys Gly Thr
 1               5                  10                  15

Ser Cys Lys Cys Ser Asn Cys Gln Cys Ala Cys Lys Lys Ser Cys
            20                  25                  30

Cys Ser Cys Cys Pro Ser Gly Cys Ser Lys Cys Ala Ser Gly Cys Val
            35                  40                  45

Cys Lys Gly Asp Thr Cys Asp Ser Lys Cys Cys Gln
 50                  55                  60

<210> SEQ ID NO 16
<211> LENGTH: 62
<212> TYPE: PRT
<213> ORGANISM: Xenopus laevis

<400> SEQUENCE: 16

Met Asp Pro Gln Asp Cys Lys Cys Glu Thr Gly Ala Ser Cys Ser Cys
```

```
                1               5                      10                     15
        Gly Thr Thr Cys Ser Cys Ser Asn Cys Lys Cys Thr Ser Cys Lys Lys
                       20                     25                     30
        Ser Cys Cys Ser Cys Cys Pro Ala Glu Cys Ser Lys Cys Ser Gln Gly
                35                     40                     45
        Cys His Cys Glu Lys Gly Ser Lys Cys Ser Cys Asn
                50                     55                     60
```

<210> SEQ ID NO 17
<211> LENGTH: 71
<212> TYPE: PRT
<213> ORGANISM: Mytilus edulis

<400> SEQUENCE: 17

```
        Pro Gly Pro Cys Asn Cys Ile Glu Thr Asn Val Cys Ile Cys Gly Thr
        1               5                      10                     15
        Gly Cys Ser Gly Lys Cys Cys Arg Cys Gly Asp Ala Cys Lys Cys Ala
                       20                     25                     30
        Ser Gly Cys Gly Cys Ser Gly Cys Lys Val Val Cys Lys Cys Ser Gly
                35                     40                     45
        Thr Cys Lys Cys Gly Cys Asp Cys Thr Gly Pro Thr Asn Cys Lys Cys
                50                     55                     60
        Glu Ser Gly Cys Ser Cys Lys
        65                     70
```

<210> SEQ ID NO 18
<211> LENGTH: 68
<212> TYPE: PRT
<213> ORGANISM: Lytechinus pictus

<400> SEQUENCE: 18

```
        Met Pro Gly Pro Asp Val Lys Cys Phe Cys Cys Arg Asp Gly Lys Glu
        1               5                      10                     15
        Cys Ala Cys Gly Gly Glu Cys Cys Ile Thr Gly Lys Cys Cys Lys
                       20                     25                     30
        Glu Gly Asp Arg Thr Cys Cys Gly Lys Cys Ser Asn Ala Ala Cys Lys
                35                     40                     45
        Cys Ala Asp Gly Cys Lys Cys Glu Gly Ala Cys Ala Cys Thr Met Gly
                50                     55                     60
        Asn Cys Thr Cys
        65
```

<210> SEQ ID NO 19
<211> LENGTH: 43
<212> TYPE: PRT
<213> ORGANISM: Drosophila melanogaster

<400> SEQUENCE: 19

```
        Met Val Cys Lys Gly Cys Gly Thr Asn Cys Gln Cys Ser Ala Gln Lys
        1               5                      10                     15
        Cys Gly Asp Asn Cys Ala Cys Asn Lys Asp Cys Gln Cys Val Cys Lys
                       20                     25                     30
        Asn Gly Pro Lys Asp Gln Cys Cys Ser Asn Lys
                35                     40
```

<210> SEQ ID NO 20
<211> LENGTH: 62
<212> TYPE: PRT
<213> ORGANISM: Caenorhabditis elegans

```
<400> SEQUENCE: 20

Val Cys Lys Cys Asp Cys Lys Asn Gln Asn Cys Ser Cys Asn Thr Gly
1               5                   10                  15

Thr Lys Asp Cys Asp Cys Ser Asp Ala Lys Cys Glu Gln Tyr Cys
            20                  25                  30

Cys Pro Thr Ala Ser Glu Lys Lys Cys Cys Lys Ser Gly Cys Ala Gly
            35                  40                  45

Gly Cys Lys Cys Ala Asn Cys Glu Cys Ala Gln Ala His
        50                  55                  60

<210> SEQ ID NO 21
<211> LENGTH: 74
<212> TYPE: PRT
<213> ORGANISM: Oryza sativa

<400> SEQUENCE: 21

Met Ser Cys Ser Cys Gly Ser Ser Cys Ser Cys Gly Ser Asn Cys Ser
1               5                   10                  15

Cys Gly Lys Lys Tyr Pro Asp Leu Glu Glu Lys Ser Ser Ser Thr Lys
            20                  25                  30

Ala Thr Val Val Leu Gly Val Ala Pro Glu Lys Lys Ala Gln Gln Phe
            35                  40                  45

Glu Ala Ala Ala Glu Ser Gly Glu Thr Ala His Gly Cys Ser Cys Gly
        50                  55                  60

Ser Ser Cys Arg Cys Asn Pro Cys Asn Cys
65                  70

<210> SEQ ID NO 22
<211> LENGTH: 75
<212> TYPE: PRT
<213> ORGANISM: Triticum aestivum

<400> SEQUENCE: 22

Met Ser Cys Asn Cys Gly Ser Gly Cys Ser Cys Gly Ser Asp Cys Lys
1               5                   10                  15

Cys Gly Lys Met Tyr Pro Asp Leu Thr Glu Gln Gly Ser Ala Ala Ala
            20                  25                  30

Gln Val Ala Ala Val Val Val Leu Gly Val Ala Pro Glu Asn Lys Ala
            35                  40                  45

Gly Gln Phe Glu Val Ala Ala Gly Gln Ser Gly Glu Gly Cys Ser Cys
        50                  55                  60

Gly Asp Asn Cys Lys Cys Asn Pro Cys Asn Cys
65                  70                  75

<210> SEQ ID NO 23
<211> LENGTH: 62
<212> TYPE: PRT
<213> ORGANISM: Candida glabrata

<400> SEQUENCE: 23

Ala Asn Asp Cys Lys Cys Pro Asn Gly Cys Ser Cys Pro Asn Cys Ala
1               5                   10                  15

Asn Gly Gly Cys Gln Cys Gly Asp Lys Cys Glu Cys Lys Lys Gln Ser
            20                  25                  30
```

```
-continued

Cys His Gly Cys Gly Glu Gln Cys Lys Cys Gly Ser His Gly Ser Ser
        35                  40                  45

Cys His Gly Ser Cys Gly Cys Gly Asp Lys Cys Glu Cys Lys
    50              55                  60
```